US009044355B2

(12) United States Patent
Rana et al.

(10) Patent No.: US 9,044,355 B2
(45) Date of Patent: Jun. 2, 2015

(54) ABSORBENT ARTICLE

(76) Inventors: Amar Pal Singh Rana, Sunnyvale, CA (US); Nirmal Singh, Sunnyvale, CA (US)

( * ) Notice: Subject to any disclaimer, the term of this patent is extended or adjusted under 35 U.S.C. 154(b) by 819 days.

(21) Appl. No.: 10/264,990

(22) Filed: Oct. 4, 2002

(65) Prior Publication Data

US 2004/0068245 A1     Apr. 8, 2004

(51) Int. Cl.
| A61F 13/15 | (2006.01) |
| A61F 13/472 | (2006.01) |
| A61F 13/47 | (2006.01) |
| A61F 13/535 | (2006.01) |
| A61F 13/84 | (2006.01) |
| A61F 13/53 | (2006.01) |

(52) U.S. Cl.
CPC ........... *A61F 13/47218* (2013.01); *A61F 13/47* (2013.01); *A61F 13/472* (2013.01); *A61F 2013/8497* (2013.01); *A61F 13/47236* (2013.01); *A61F 13/535* (2013.01); *A61F 13/84* (2013.01); *A61F 2013/530802* (2013.01)

(58) Field of Classification Search
CPC . A61F 2/50; A61F 2002/5001; A61F 5/0096; A61F 13/47; A61F 13/4702; A61F 13/472; A61F 13/47236; A61F 13/84; A61F 2013/4708; A61F 2013/8497
USPC ............. 604/385.01–385.04, 385.06, 385.14, 604/385.17, 387; 434/273; 600/38; 623/66.1
See application file for complete search history.

(56) References Cited

U.S. PATENT DOCUMENTS

| 4,627,111 | A | * | 12/1986 | Storie .................................. 2/69 |
| 4,631,062 | A | * | 12/1986 | Lassen et al. ............ 604/385.02 |
| 4,804,380 | A |   | 2/1989 | Lassen et al. |
| 5,011,480 | A | * | 4/1991 | Gossens et al. .......... 604/385.23 |
| 5,171,302 | A | * | 12/1992 | Buell ........................ 604/385.23 |
| 5,285,531 | A | * | 2/1994 | Nalbandian ....................... 2/106 |
| 5,324,278 | A |   | 6/1994 | Visscher et al. |
| 5,591,150 | A | * | 1/1997 | Olsen et al. .............. 604/385.23 |
| 6,152,905 | A |   | 11/2000 | Osborn, III et al. |
| 6,171,291 | B1 |  | 1/2001 | Osborn, III et al. |
| 6,316,688 | B1 | * | 11/2001 | Hammons et al. ............ 604/378 |
| 6,350,258 | B1 | * | 2/2002 | Markowiecki ......... 604/385.201 |
| 6,387,084 | B1 |  | 5/2002 | Van Gompel et al. |
| 6,406,648 | B1 | * | 6/2002 | Noel et al. .................... 264/46.4 |
| 6,575,948 | B1 | * | 6/2003 | Kashiwagi et al. .... 604/385.101 |
| 6,740,069 | B2 | * | 5/2004 | Drevik ...................... 604/385.01 |

FOREIGN PATENT DOCUMENTS

EP          888763 A1 *   1/1999   ............. A61F 13/15

OTHER PUBLICATIONS

Takatoshi Kobayashi "Utilization of water absorbent polymers in hygenic field", Zairyo Gijutsu, 6(9) 361-365 1988 with translation.

* cited by examiner

*Primary Examiner* — Lynne Anderson

(57) ABSTRACT

An absorbent article to absorb and contain human female bodily excretions from the genitalia for placement in the inner crotch portion of an undergarment of a human female wearer; and with a separate cosmetic human female crotch enhancer element which is positioned on garment faceable side and gives the simulated appearance of exaggerated contours and curves associated with the human female external genitalia with the simulated appearance of exaggerated pudendal cleft associated with the human female external genitalia and without or with the simulated pubic hair to provide the human female wearer with subtle understated sexual expression and subtle non-verbal communication.

7 Claims, 27 Drawing Sheets

ABSORBENT ARTICLE

BACKGROUND OF THE INVENTION

1. Technical Field

The present invention pertains to absorbent articles, such as sanitary napkins, pantiliners, panty shields, incontinent pads and interlabial devices that are designed to absorb and contain menstrual fluids and other human female body exudates from the pudendal region and to prevent body and clothing soiling. The present invention particularly relates to absorbent articles to provide the wearer with subtle understated sexual expression or subtle non-verbal communication, short of exposing themselves when viewed on the outer crotch surface of a human female wearer's undergarments or outer garments of every day dress or casual usage or tight fitting clothing, body suits, swim suits, leotard, sports tights, or similarly thin or close-fitting outer garments and the like.

2. Glossary of Terms

The term "absorbent article", as used herein, refers to articles such as sanitary napkins, panty liners, panty shields, incontinent pads which absorb and contain human female body exudates with various styles such as without or with flaps, hump on the body faceable side, various conforming styles of human female body authentic external genitalia and the like or interlabial absorbent articles which fit into the human female genitalia's interlabial space.

The human female "genitalia" or "external genitalia" is a collective term used to describe the visible external human female genital region extending from the mons pubis to the perenium.

The "intersection" of the separate cosmetic human female crotch enhancer element with the rest of the absorbent article refers to a surface parallel to the garment faceable side of the absorbent article and may have any random encircled shape or the shape of a circle, oval, trapezoid, rectangle, triangle, pentagon, or hexagon.

The term "longitudinal medial hump" refers to a narrow volume centered along the longitudinal centerline of the absorbent article and provides additional absorbent capacity and liquid acquisition capability and preferably maintains the absorbent article in close physical contact with the human female wearer's body, particularly the inward-faceable surfaces of the wearer's labia majora. It also provides the absorbent article with a centering/positioning mechanism. The hump forming volume is preferably a compressible and resilient material. The hump forming volume may comprise a material that is different from the material used in the absorbent core. The compressibility allows the hump (or a least partially the top portion of the hump faceable the wearer's body) to narrow and fit comfortably in the space between the human female wearer's labia. The resiliency allows the hump to better conform to the human female wearer's body and maintain such contact during the wear. The hump forming volume is both wet and dry resilient so as to provide the resistance to collapsing under the conditions encountered during the wear.

The term "pudendal region" refers to the externally visible female genitalia and is limited to labia majora, labia minora, the clitoris, and the vestibule.

The term "interlabial space" refers to that space of the female anatomy which is located between the inside surfaces of the labia majora extending into the vestibule. Located within the interlabial space are the labia minor, the vestibule and the principal urogenital members including the clitoris, the orifice of the urethra, and the orifice of the vagina. Standard medical authorities teach that the vestibule refers to the space bounded laterally by the inside surfaces of the labia minora and extending interiorly to the floor between the clitoris and the orifice of the vagina. The interlabial space for the purposes of the present description does not extend substantially beyond the orifice of the vagina into the vaginal interior.

The "inward-faceable" surfaces of the labia majora are those surfaces of the labia majora adjacent the space between the labia majora associated with the human female external genitalia.

The term "sanitary napkin", as used herein, refers to an article which is worn by females adjacent to the genitalia and which is intended to absorb and contain the various exudates which are discharged from the body (e.g., blood, menses, and urine). Interlabial devices which are reside partially within and partially external of the wearer's vestibule are also within the scope of this invention.

The term "separate volume" refers to a separate cosmetic human female crotch enhancer element positioned on the garment faceable side which gives a simulated appearance of exaggerated contours and curves associated with human female external genitalia with a pudendal cleft associated with a human female external genitalia; or with the simulated appearance of the exaggerated pudendal cleft associated with the human female external genitalia with any one combination of labia majora as if spread open manually or labia majora as if the human female's thighs appear to be are far apart or as if labia majora is not spread open, labia minora, clitoris, clitoral hood and other externally visible parts of the female genitalia within the pudendal cleft as they appear to project out of the labia majora starting from anterior commissure of labia majora to posterior commissure of labia majora or part thereof associated with the human female external genitalia; without or with the simulated pubic hair on the garment faceable side of the said cosmetic human female crotch enhancer element.

3. Description of the Related Art

Absorbent articles, such as sanitary napkins, pantiliners, panty shields, incontinent pads and interlabial devices that are designed to absorb and/or contain menstrual fluids and other human female body exudates from the pudendal region and to prevent body and clothing soiling are well known.

U.S. Pat. No. 6,387,084 issued to VanGompel, et. al. on May 14, 2002 entitled, "Sanitary Napkin With Garment Attachment Panels" describes an elongated sanitary napkin with garment attachment panels. The form and construction of the absorbent pad is generally conventional. In preparation for use, the peel strip is removed from the absorbent pad exposing the garment adhesive and absorbent article is centered and mounted on the crotch portion of an undergarment in the usual way: There is no focus on providing the simulated appearance of exaggerated curves and contours associated with the human female's external genitalia.

U.S. Pat. No. 6,392,117 issued to Mayer, et. al on May 21, 2002 entitled, "Body Fitting Compound Sanitary Napkin" describe a primary absorbent member and a secondary absorbent member. Both the primary and secondary absorption surfaces contact the wearer's body for the primary purpose to receive and contain menses and other vaginal discharges. The primary absorbent layer is sized to fit at least partially within the pudendal cleft of a wearer during use. There is no focus on providing the simulated appearance of exaggerated curves and contours associated with the human female's external genitalia.

U.S. Pat. No. 4,518,451 issued to Luceri, et. al on May 21, 1985 entitled, "Embossed Panty Liner" focus on pleasing embossed patterns such as flowers, lines, spots and the like, on the body faceable surface and longitudinal edges. There is no focus on providing the simulated appearance of exaggerated curves and contours associated with the human female's external genitalia.

U.S. Pat. No. 6,406,648 issued to Noel, et. al. on Jun. 18, 2002 entitled, "Method Of Making Shaped Foam Implements" describes a three dimensional foam implement with the focus is on conforming to the female pudendal region. There is no focus on providing the simulated appearance of exaggerated curves and contours associated with the human female's external genitalia.

U.S. Pat. No. 6,171,291 issued to Osborn, III, et. al. on Jan. 9, 2001 entitled, "Generally Thin, Flexible, Sanitary Napkin With Central Absorbent Hump" describes a sanitary napkin with a longitudinal medial hump for centering/positioning mechanism and better contact and conforming to the shape of the wearer's body, particularly with the "inward-faceable surfaces" of the wearer's labia majora. In one embodiment, the absorbent article may comprise a sanitary napkin having an absorbent core that separates from the backsheet of the sanitary napkin The separation of the absorbent core from the backsheet accommodates the independence of movement between the body of the wearer and the wearer's undergarments. In an alternative embodiment, the sanitary napkin is provided with a panty fastner having a configuration that allows the portion of a sanitary napkin containing the hump to separate from the wearer's undergarments to accommodate the independence of movement between the body of the wearer and the wearer's undergarments. In another embodiment, the sanitary napkin may have a traversely segmented hump adapted to better conform to the body of the wearer. In still another embodiment, the sanitary napkin may be extensible in the longitudinal direction, the lateral direction, or both. There is no focus on providing the simulated appearance of exaggerated curves and contours associated with the human female's external genitalia.

U.S. Pat. No. 4,804,380 issued to Lassen, et. al. on Feb. 14, 1989 entitled, "Anatomically Shaped, Self-Aligning, Sanitary Protection Device" describes a sanitary napkin where the forward portion of this device is flattened to cover the externally the area of the mons pubis and the area exterior to the clitoris. The back portion of this device is formed in a peak like shape which readily adjusts to and molds to the inverted V-shape of the rear portion of the labia, the perineum and the forward portion of the area between buttocks. There is no focus on providing the simulated appearance of exaggerated curves and contours associated with the human female's external genitalia.

U.S. Pat. No. 5,324,278 issued to Visscher, et. al. on Jun. 28, 1994 entitled, "Sanitary Napkin Having Components Capable Of Separation In Use" describes a sanitary napkin where the components it is comprised of may separate in relation to other components of the sanitary napkin to accommodate the independence of movement between the body of the wearer and the wearer's undergarments. There is no focus on providing the simulated appearance of exaggerated curves and contours associated with the human female's external genitalia.

U.S. Pat. No. 6,261,271 B1 issued to Osborn, III, et. al. on Jul. 17, 2001 entitled, "Absorbent Interlabial Device" describes an absorbent interlabial device that is worn interlabially for catamenial purposes, incontinence protection, or both. There is no focus on providing the simulated appearance of exaggerated curves and contours associated with the human female's external genitalia.

None of the references suggest the usage of absorbent articles to provide the human female wearer with subtle understated sexual expression or subtle non-verbal communication, short of exposing themselves when viewed on the outer crotch surface of a human female wearer's undergarments or outer garments of every day dress or casual usage or tight fitting clothing, body suits, swim suits, leotard, sports tights, or similarly thin or close-fitting outer garments and the like.

SUMMARY OF THE INVENTION

There exists a need for an absorbent article or interlabial device with an integral or separate volume which is at least partially or wholly formed by a cosmetic human female crotch enhancer element positioned on the garment faceable side or positioned on or within any combination of body faceable side, garment faceable side and absorbent element of the absorbent article which gives the simulated appearance of exaggerated contours and curves associated with the human female external genitalia without the pudendal cleft associated with the human female external genitalia; or with the simulated appearance of the exaggerated pudendal cleft associated with the human female external genitalia with all or any combination of labia majora as if spread open manually, or labia majora as if the human female's thighs appear to be are far apart or as if labia majora is not spread open, labia minora, clitoris, clitoral hood and other externally visible parts of the female genitalia within the pudendal cleft as they appear to project out of the labia majora starting from anterior commissure of labia majora to posterior commissure of labia majora or part thereof associated with the human female external genitalia without or with the simulated pubic hair on the garment faceable side of the cosmetic human female crotch enhancer element said absorbent article may be worn year round due to it's cosmetic appeal and for subtle, understated sexual signal that imparts sexual communication without being overt and a subtle simulated non-verbal communication or for personal expression, short of exposing themselves when viewed on the outer crotch surface of a human female wearer's undergarments, figure control garments or outer garments of every day dress or casual usage or tight fitting clothing, body suits, swim suits, leotard, sports tights, or similarly thin or close-fitting outer garments and the like.

It is an object of this invention to provide the human female wearer with an absorbent article to absorb and contain bodily excretions from the human female genitalia and prevent the body and clothing soiling It is an also object of this invention to provide the wearer with an absorbent article or interlabial device with cosmetic crotch enhancer element such that may be worn year round due to it's cosmetic appeal and for subtle, understated sexual signal that imparts sexual communication without being overt or a subtle simulated non-verbal communication or for personal expression, short of exposing themselves when viewed on the outer crotch surface of a human female wearer's undergarments or figure control garments or outer garments of every day dress or casual usage or tight fitting clothing, body suits, swim suits, leotard, sports tights, or similarly thin or close-fitting outer garments and the like.

It is also an object of this invention that the integral or separate cosmetic crotch enhancer element on the absorbent article or interlabial device helps due to it's resilience such that the absorbent article or interlabial device maintains sufficient integrity while it is worn such that it does not wrinkle, fold, disintegrate, tear or collapse during usage.

The absorbent article and integral or separate cosmetic human female crotch enhancer element may be scented with various aromatic scents or artificial vaginal scents preferably without the potential of adverse reaction to the wearer's genitalia to further highlight the understated sexual signal that imparts sexual communication without being overt or a subtle simulated non-verbal communication or for personal expression.

DETAILED DESCRIPTION OF THE INVENTION

The present invention pertains to absorbent articles, such as sanitary napkins, pantiliners, panty shields, incontinent pads and interlabial devices that are designed to absorb and contain menstrual fluids and other human female body exudates from the human female genitalia and to prevent body and clothing soiling. The present invention particularly relates to absorbent articles to provide the wearer with subtle understated sexual expression or subtle non-verbal communication, short of exposing themselves when viewed on the outer crotch surface of a human female wearer's undergarments or outer garments of every day dress or casual usage or tight fitting clothing, body suits, swim suits, leotard, sports tights, or similarly thin or close-fitting outer garments and the like.

The present invention pertains to absorbent articles to absorb and contain human female bodily excretions from the human female genitalia of the type for placement in the inner crotch portion of an undergarment which comprises of an absorbent element having a body faceable side, a fully or partially covered impervious garment faceable side, longitudinally extending edges, traverse ends without flaps or with flaps extending from each of said longitudinal edges, or an absorbent article to absorb and contain bodily excretions from the human female genitalia of the type insertable into the interlabial space of a human female wearer; and such absorbent article with an integral or separate volume which is at least partially or wholly formed by a cosmetic human female crotch enhancer element positioned on the garment faceable side or positioned on or within any combination of body faceable side, garment faceable side and absorbent element of the absorbent article which gives the simulated appearance of exaggerated contours and curves associated with the human female external genitalia without the pudendal cleft associated with the human female external genitalia; or with the simulated appearance of the exaggerated pudendal cleft associated with the human female external genitalia with all or any combination of labia majora as if spread open manually or as if the human female's thighs are far apart or as if labia majora is not spread open, labia minora, clitoris, clitoral hood and other externally visible parts of the female genitalia within the pudendal cleft as they appear to project out of the labia majora starting from anterior commissure of labia majora to posterior commissure of labia majora or part thereof associated with the human female external genitalia without or with the simulated pubic hair on the garment faceable side of the cosmetic human female crotch enhancer element.

Figure 1:
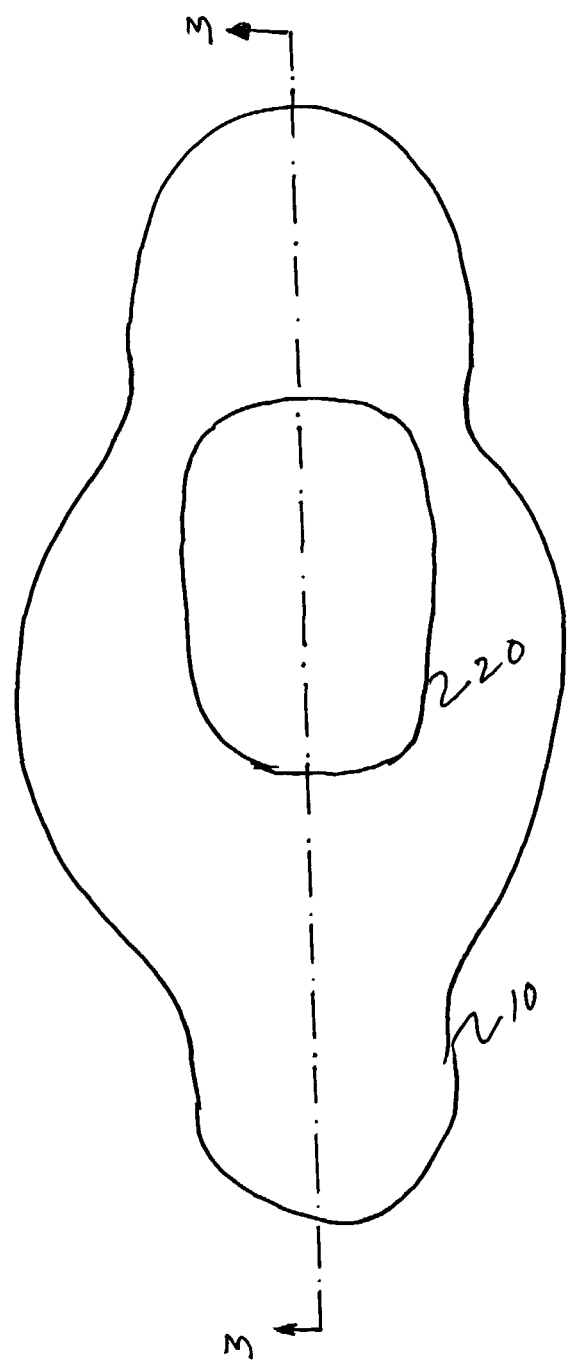
FIG. 1 is a top plan view of the garment faceable side of an embodiment of the present invention.
Figure 2:
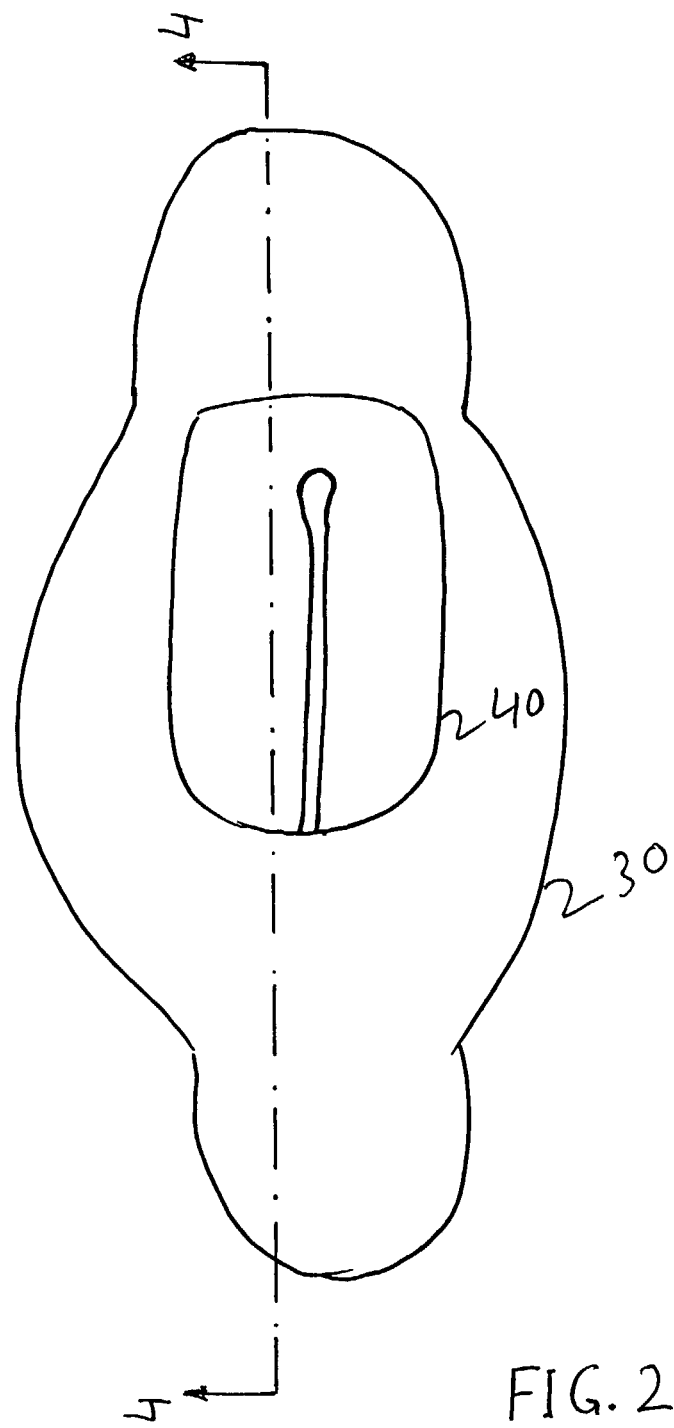
FIG. 2 is a top plan view of the garment faceable side of another embodiment of this invention showing the exaggerated pudendal cleft.
Figure 3:
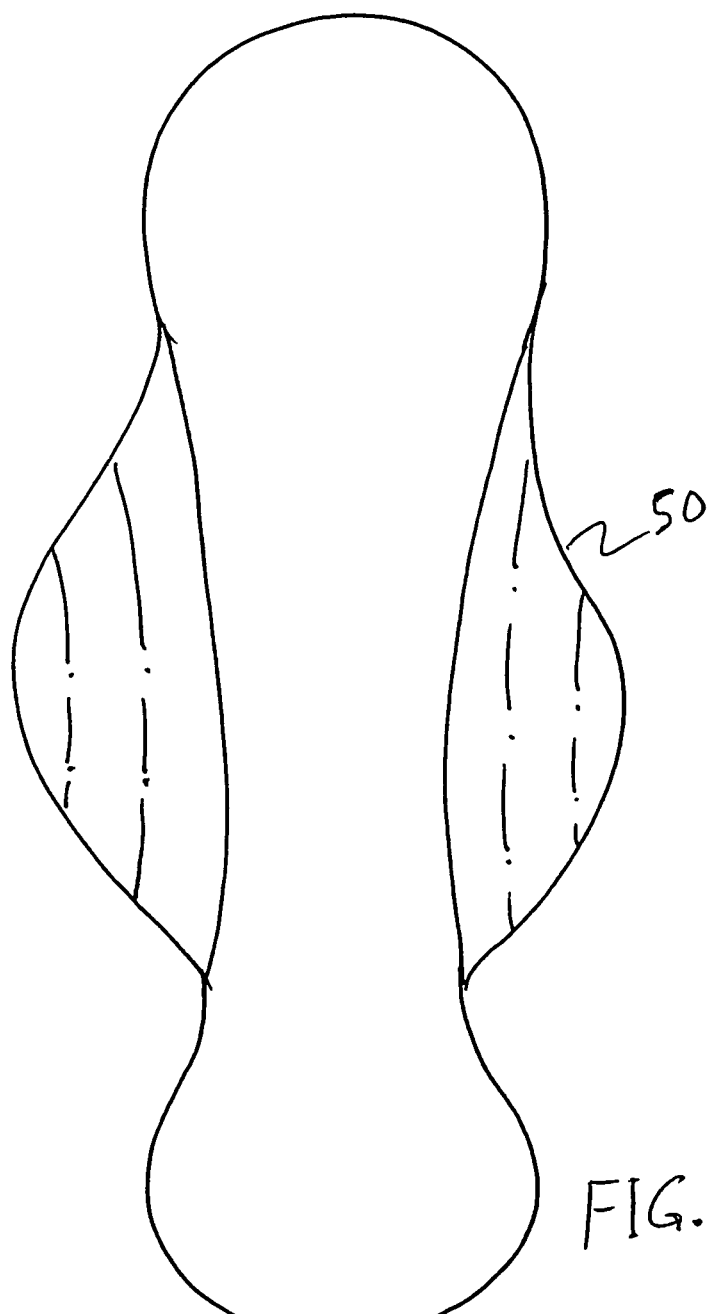
FIG. 3 is a top plan view of prior art related to the present invention.

FIG. 1 is the top plan view of the garment faceable side of an embodiment of the present invention. Item 10 is the absorbent article with an integral cosmetic female crotch enhancer element as item 20 without the exaggerated pudendal cleft of the female wearer. FIG. 2 is a top plan view of the garment faceable side of another embodiment of this invention. Item 30 is the absorbent article with an integral cosmetic crotch enhancer element as item 40 with exaggerated pudendal cleft of a female wearer. FIG. 3 is a top plan view of prior art related to the present invention showing a sanitary napkin with flaps as item 50.

Figure 4:
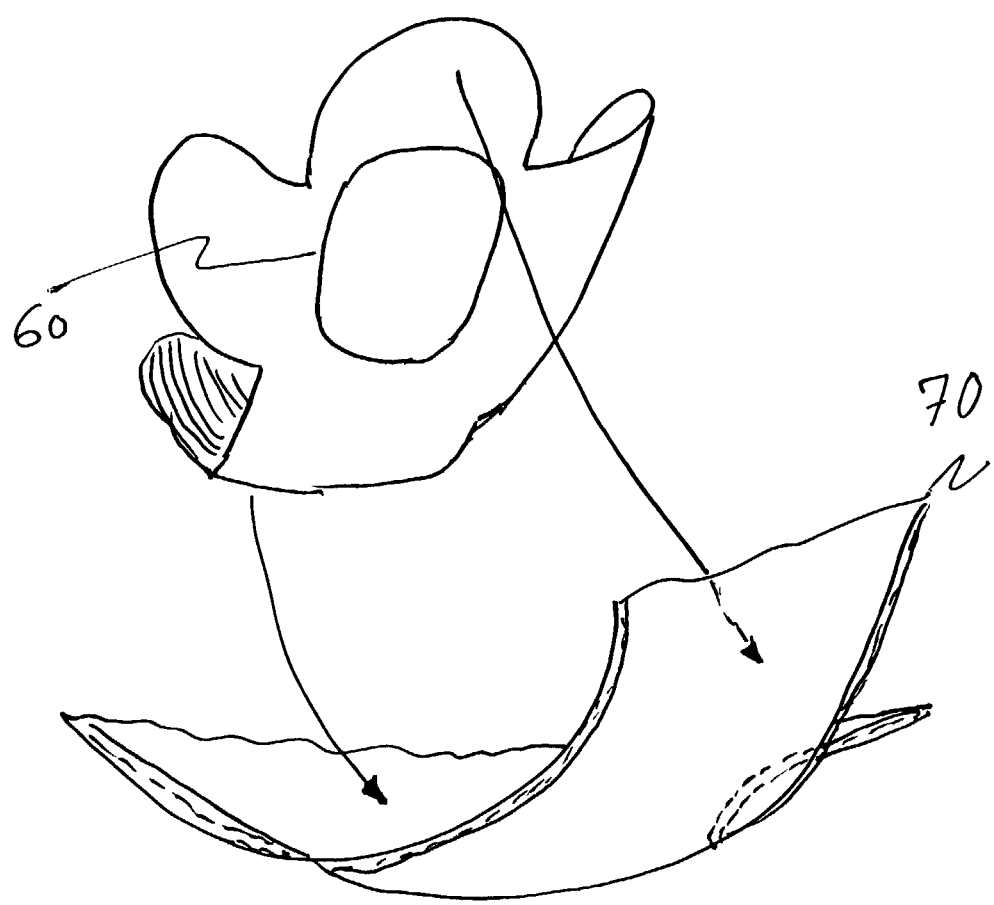
FIG. 4 is a perspective, schematic illustration of the placement of the sanitary napkin with an integral cosmetic crotch enhancer element onto the inner crotch portion of the undergarment corresponding to FIG. 1.
Figure 5:
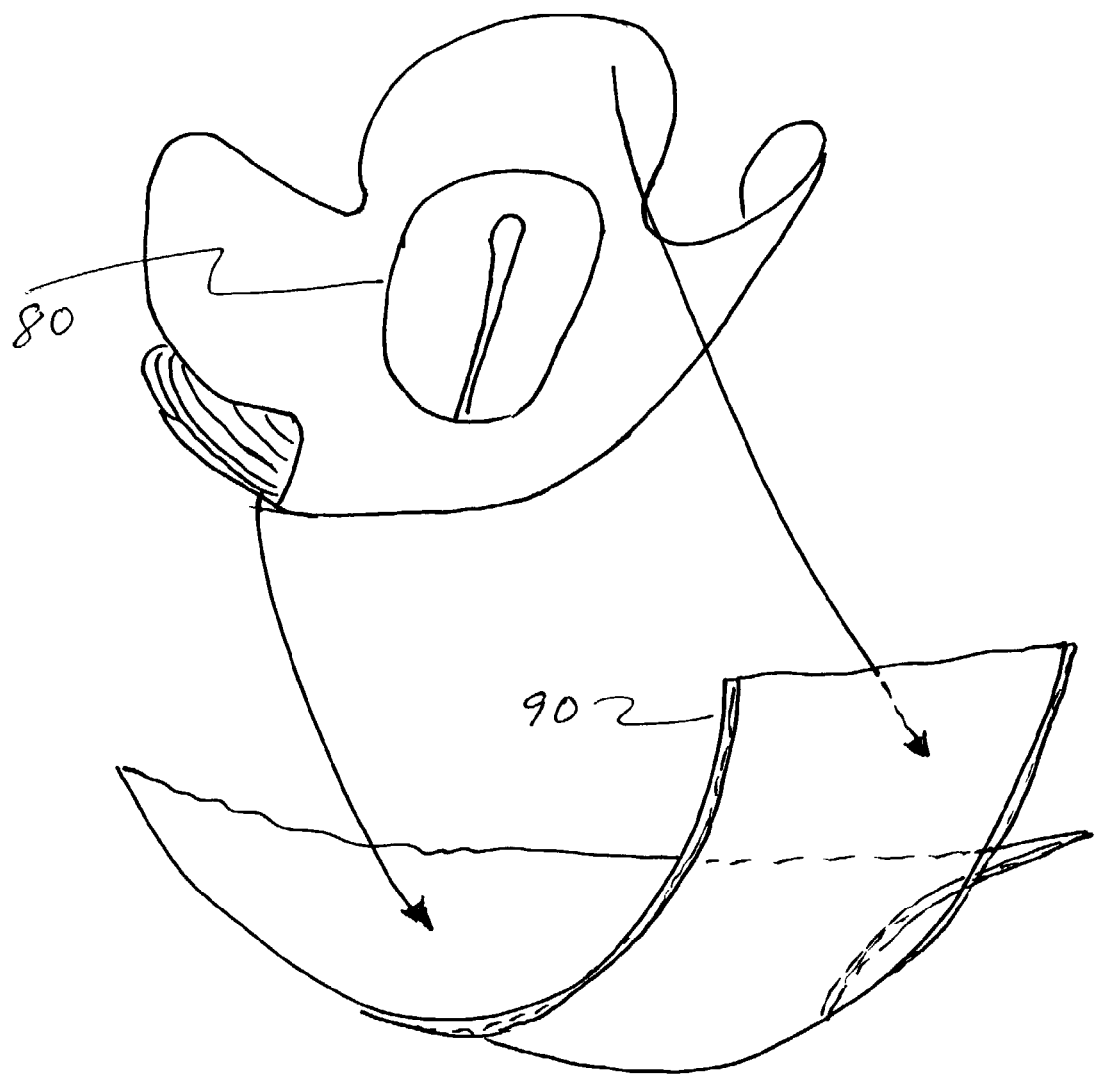
FIG. 5 is a perspective, schematic illustration of the placement of the sanitary napkin with an integral cosmetic crotch enhancer element showing the exaggerated pudendal cleft onto the inner crotch portion of the undergarment corresponding to FIG. 2.

FIG. 4 is a perspective, schematic illustration of the placement of the sanitary napkin with flaps with an integral cosmetic crotch enhancer element without the exaggerated pudendal cleft onto the inner crotch portion of the undergarment as item 70 corresponding to FIG. 1. The integral cosmetic crotch enhancer element as item 60 may optionally have adhesive on the garment faceable side. FIG. 5 is a perspective, schematic illustration of the placement of the sanitary napkin with flaps with an integral cosmetic crotch enhancer element with the exaggerated pudendal cleft as item 80 onto the inner crotch portion of the undergarment as item 90 corresponding as item 40 to FIG. 2. The integral cosmetic crotch enhancer element with exaggerated pudendal cleft as item 80 may optionally have adhesive on the garment faceable side.

Figure 6:
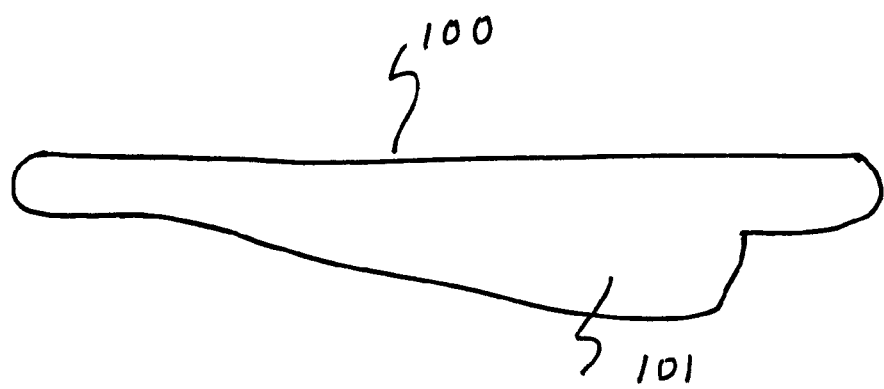
FIG. 6 is a cross-sectional view taken along longitudinal line 3-3 of FIG. 1 or along longitudinal line 4-4 of FIG. 2 illustrating the increased volume of the absorbent due to the cosmetic crotch enhancer element.
Figure 7:
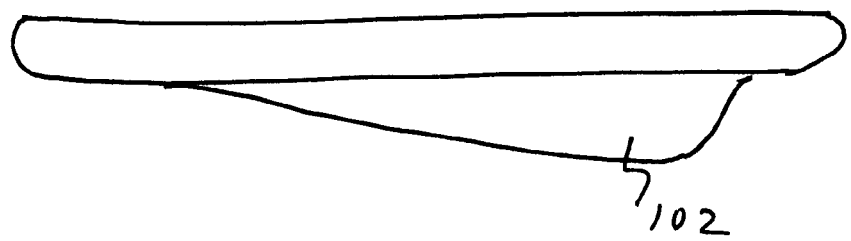
FIG. 7 is a cross-sectional view taken along longitudinal line 3-3 of FIG. 1 or along longitudinal line 4-4 of FIG. 2 illustrating no increased volume of the absorbent due to the cosmetic crotch enhancer element as still another embodiment.

FIG. 6 is a cross-sectional view taken along longitudinal line 3-3 of FIG. 1 or along longitudinal line 4-4 of FIG. 2 with item 100 depicting the body faceable side of the absorbent article and illustrating the increased volume of the absorbent due to the cosmetic crotch enhancer element as item 101. FIG. 7 is a cross-sectional view taken along longitudinal line 3-3 of FIG. 1 or along longitudinal line 4-4 of FIG. 2 illustrating no increased volume of the absorbent due to the cosmetic crotch enhancer element as item 102 as still another embodiment.

Figure 8:
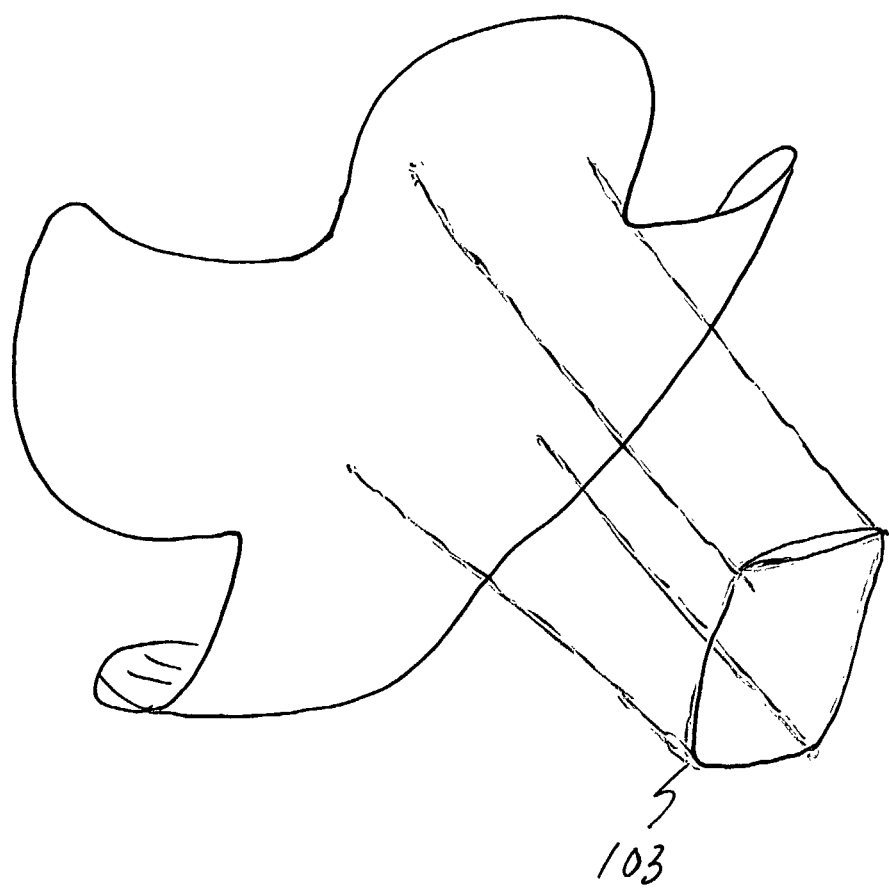
FIG. 8 is a perspective, schematic illustration of the placement of the separate cosmetic crotch enhancer element as still another embodiment on to the garment faceable side of a conventional sanitary napkin.
Figure 9:
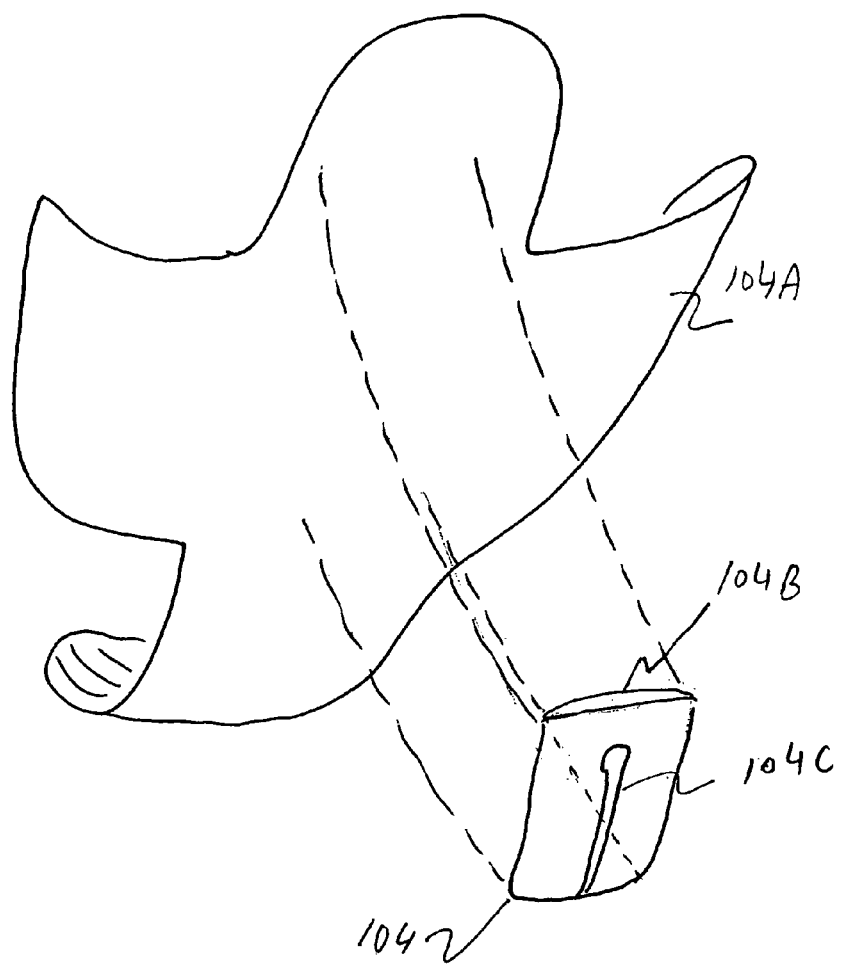
FIG. 9 is a perspective, schematic illustration of the placement of the separate cosmetic crotch enhancer element showing the exaggerated pudendal cleft as still another embodiment on to the garment faceable side of a conventional sanitary napkin.

FIG. 8 is a perspective, schematic illustration of the placement of the separate cosmetic crotch enhancer element without the exaggerated pudendal cleft as item 103 as still another embodiment on to the garment faceable side of a conventional sanitary napkin. Item 103 may optionally have adhesive on the garment faceable side as well optionally on the sanitary napkin side. The wearer may adjust the appropriate placement of item 103 so as to superimpose upon the human female wearer's authentic external genitalia or howsoever the wearer may desire for the personal or sexual expression of the wearer. FIG. 9 is a perspective, schematic illustration of the placement of the separate cosmetic crotch enhancer element with the exaggerated pudendal cleft as item 104 as still another embodiment on to the garment faceable side of a conventional sanitary napkin. Item 104 may optionally have adhesive on the garment faceable side as well optionally on the sanitary napkin faceable side. The wearer may adjust the appropriate placement of item 104 so as to superimpose upon the human female wearer's pudendal cleft or howsoever the wearer may desire for the personal or sexual expression of the wearer. Item 104A in FIG. 9 shows the fully covered impervious garment faceable side of the absorbent article with item 104B showing the adhesive to attach item 104 which is the separate cosmetic human female crotch enhancing element to the remaining absorbent article. Item 104C is the pudendal cleft associated with the simulated appearance of the exaggerated contours and curves. The exaggerated contour and curves associated with item 104 are enhanced hills, enhanced valleys and enhanced cleft in the three dimensional volume of item 104, more pronounced than the corresponding human female external genitalia with a wider and deeper pudendal cleft and raised labia majora rather than just a flat or nearly flat mons pubis compared to as if a human female wearer's thighs were wide apart or a human female wearer's labia majora were to be spread open more widely manually or the exaggeration of contours and curves with the simulated appearance that the labia minora, clitoris, clitorial hood and other externally visible parts of the female genitalia within the pudendal cleft as they appear to project out of the labia majora starting from anterior commissure of labia majora to posterior commissure of labia majora even if labia majora is not separated manually. One may also attach simulated pubic hair by adhesive on the garment faceable side of item 104. Further, one may utilize an adhesive such as "Medical Adhesive" manufactured by Hollister Inc. Livertyville, Ill. or glue, adhesives and tape by 3M Corporation of Minneapolis, Minn. or instead of adhesive, one may also utilize mechanical means such as hook-and-loop fasteners from Velcro Industries having a mailing address of 406 Brown Avenue, Manchester, N.H. 03103.

Figure 10:
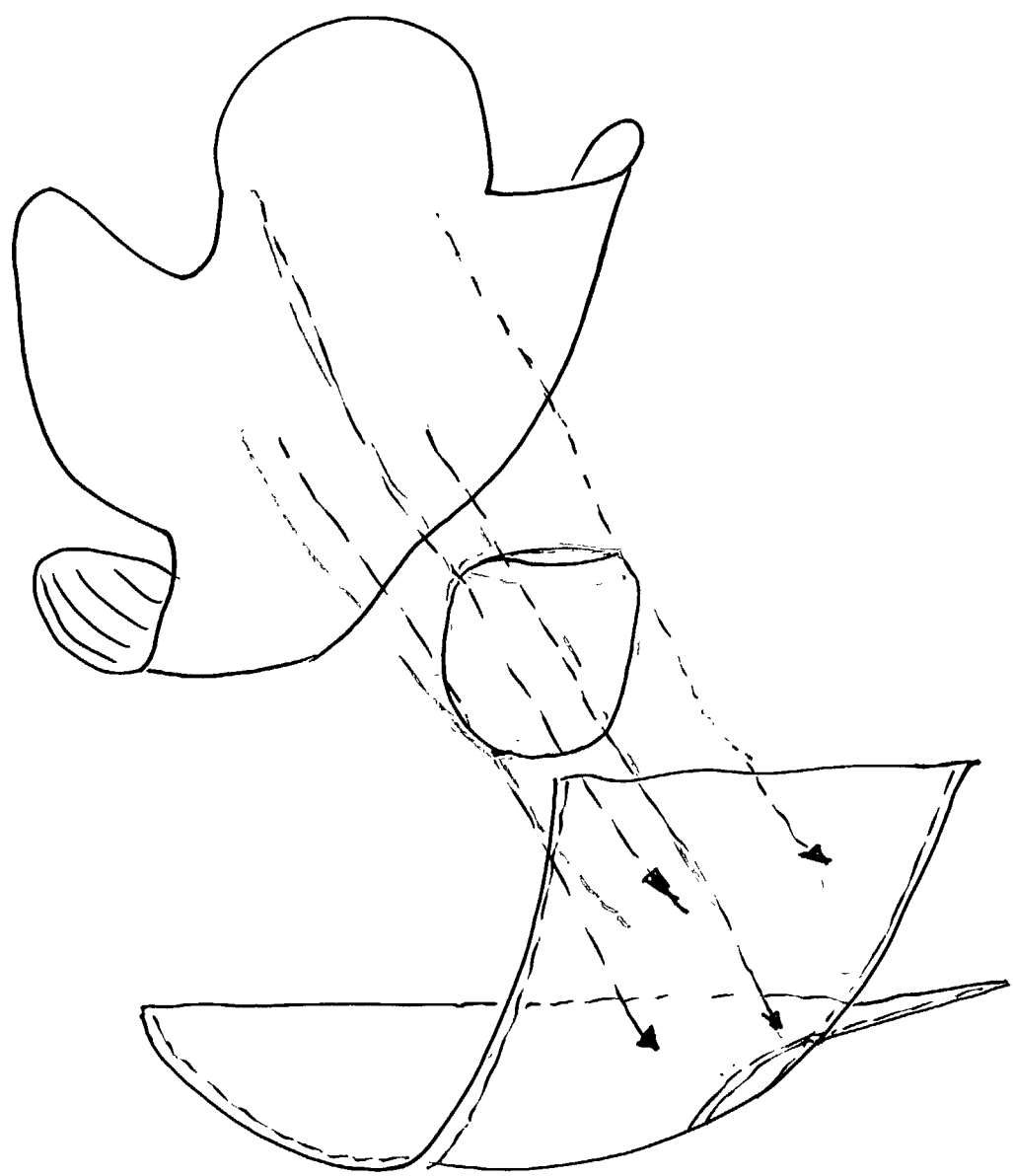
FIG. 10 is a perspective, schematic illustration of the placement of the separate cosmetic crotch enhancer element and a conventional sanitary napkin onto the inner crotch portion of the undergarment corresponding to FIG. 8.
Figure 11:
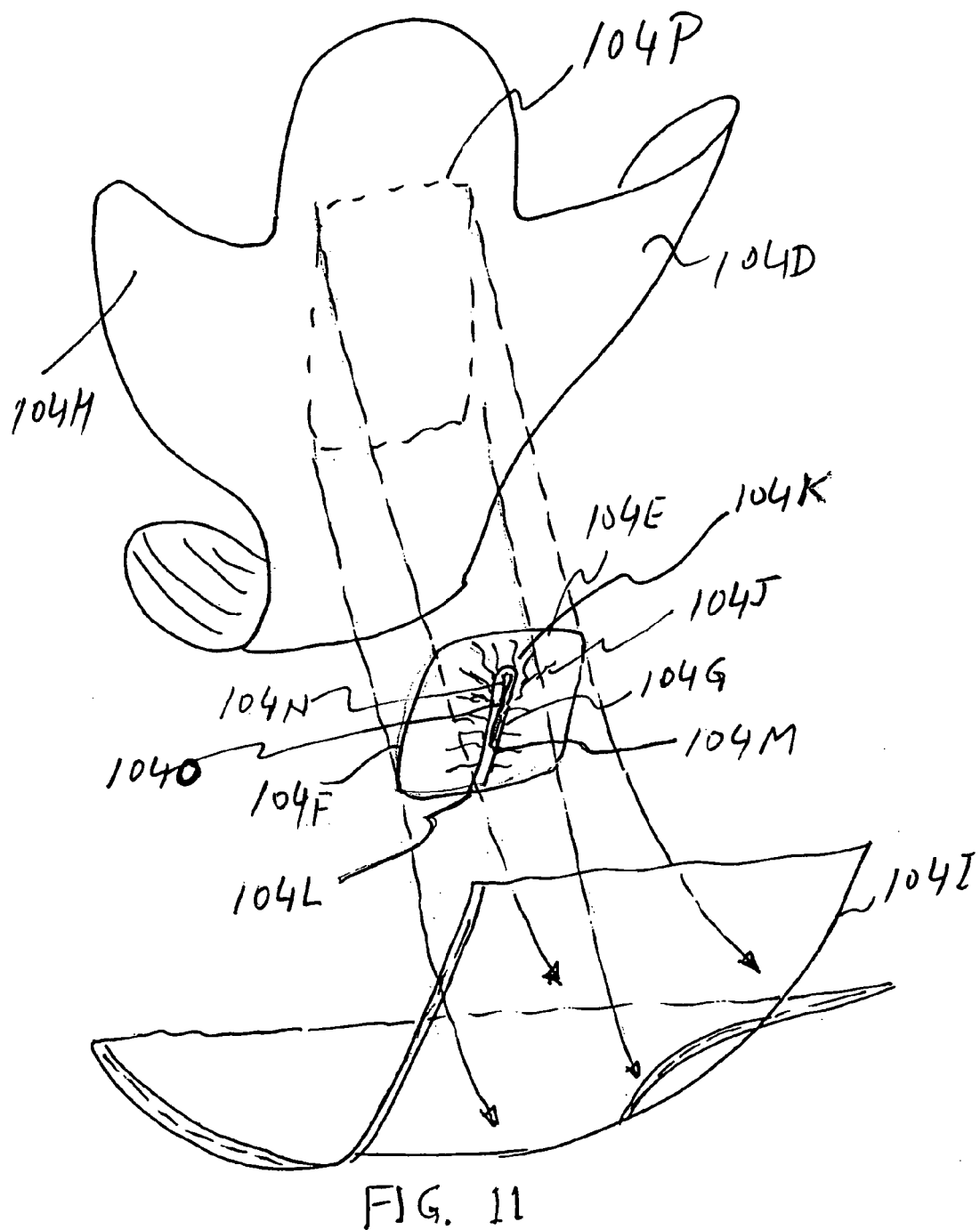
FIG. 11 is a perspective, schematic illustration of the placement of the separate cosmetic crotch enhancer element showing the exaggerated pudendal cleft and a conventional sanitary napkin onto the inner crotch portion of the undergarment corresponding to FIG. 9.

FIG. 10 is a perspective, schematic illustration of the placement of the separate cosmetic crotch enhancer element without the exaggerated pudendal cleft and a conventional sanitary napkin onto the inner crotch portion of the undergarment corresponding to item 103 of FIG. 8. FIG. 11 is a perspective, schematic illustration of the placement of the separate cosmetic crotch enhancer element with the exaggerated pudendal cleft and a conventional sanitary napkin onto the inner crotch portion of the undergarment corresponding to item 104 of FIG. 9. Item 104D in FIG. 11 shows the fully covered impervious garment faceable side of the absorbent article with item 104E showing the adhesive to attach item 104F which is the separate cosmetic human female crotch enhancing element to the remaining absorbent article. Item 104G is the pudendal cleft associated with the simulated appearance of the exaggerated contours and curves. Optionally one may have adhesive on the garment faceable side of the flaps, item 104H or optionally the adhesive may be present on the item 104D on the area not covered by item 104F or adhesive may also be present on garment facing side of item 104F for better contact of the absorbent article with the wearer's undergarments. Item 104I is the outer crotch of the wearer's undergarment. Item 104J shows the simulated pubic hair attached by adhesive on the garment faceable side. The exaggerated contour and curves associated with item 104F are enhanced hills, enhanced valleys and enhanced cleft in the three dimensional volume of item 104F, more pronounced than the corresponding human female external genitalia with a wider and deeper pudendal cleft, item 104G, and raised labia majora rather than just a flat or nearly flat mons pubis compared to as if a human female wearer's thighs were wide apart or a human female wearer's labia majora were to be spread open more widely manually or the exaggeration of contours and curves with the simulated appearance that the labia minora, item 104O, clitoris, clitorial hood, item 104N, and other externally visible parts of the female genitalia within the pudendal cleft as they appear to project out of the labia majora starting from anterior commissure, item 104K, of labia majora to posterior commissure, item 104L, of labia majora, item 104M, even if labia majora is not separated manually. One may also attach simulated pubic hair by adhesive on the garment faceable side of item 104. Item 104P shows an intersection of the separate cosmetic human female crotch enhancer element, item 104F, with the rest of the absorbent article along a surface parallel to the garment faceable side of the absorbent article may have any random encircled shape, item 104P, or the shape of a circle, oval, trapezoid, rectangle, triangle, pentagon, or hexagon. Simulated pubic hair is available from International Hairgoods, Inc. (a subsidiary of Aderans), 5909 Baker Rd., STE 505, Minnetonka, Minn. 55345. Item 104F may be made from cotton, plastic, rubber, thermoplastic or castable materials, silicone, thermosetting resins but not limited to these materials. The separate cosmetic human female crotch enhancer element's simulated and exaggerated contours and curves associated with the human female's external genitalia with the pudendal cleft can be made by the above mentioned materials providing the shapely volume by die-casting or compression or stitches in case of cotton. Further, the fully covered impervious garment faceable side, item 104D, may be made of polyolefins, e.g., polyethylene and polypropylene but not limited to these. Further, scent may be added to item 104F such as manufactured by Bigelow Chemists, Inc, NY, N.Y.

Figure 12:
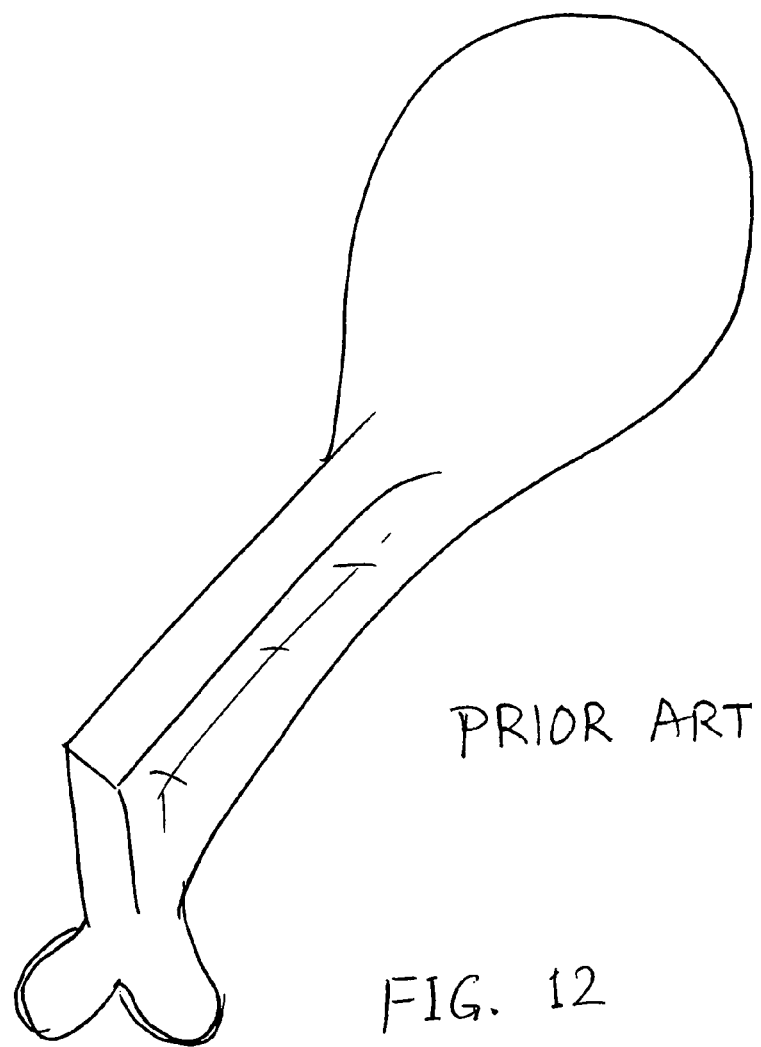
FIG. 12 is a top plan view of another prior art related to the present invention.
Figure 13:
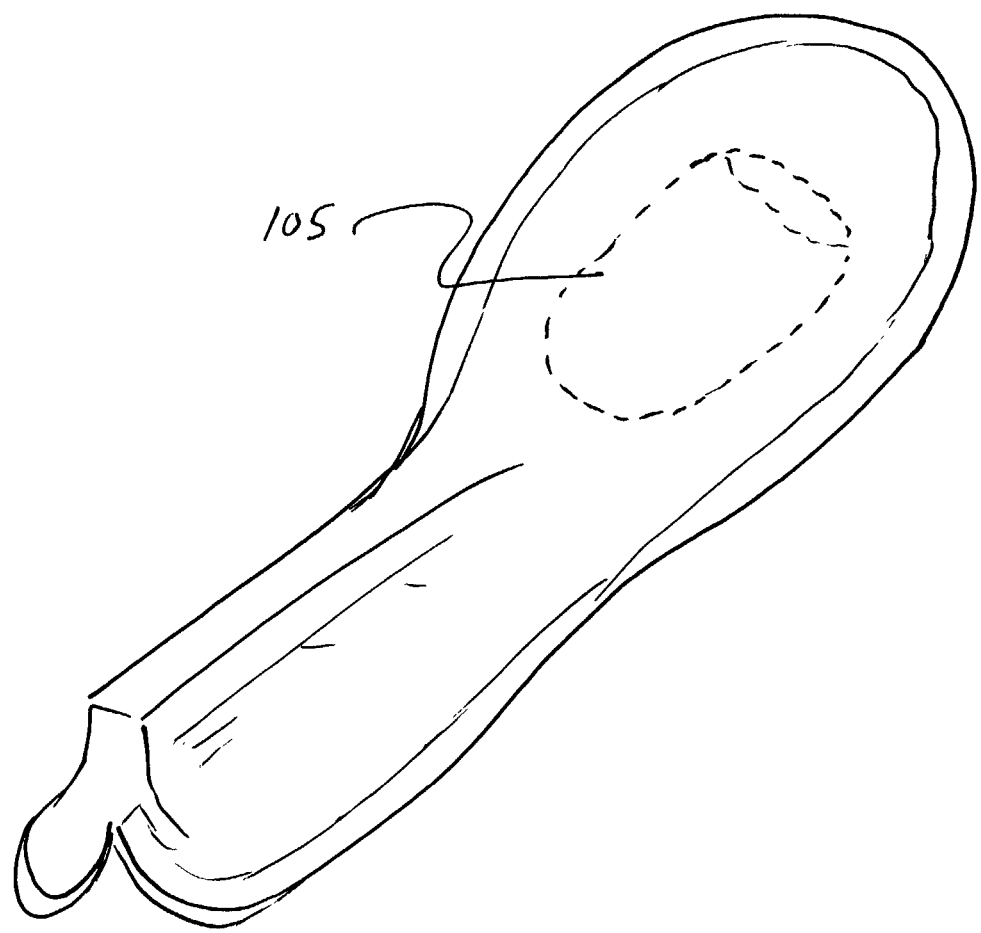
FIG. 13 is a perspective, schematic illustration of an integral or separate cosmetic crotch enhancer element on the garment faceable side of the sanitary napkin of FIG. 12.
Figure 14:
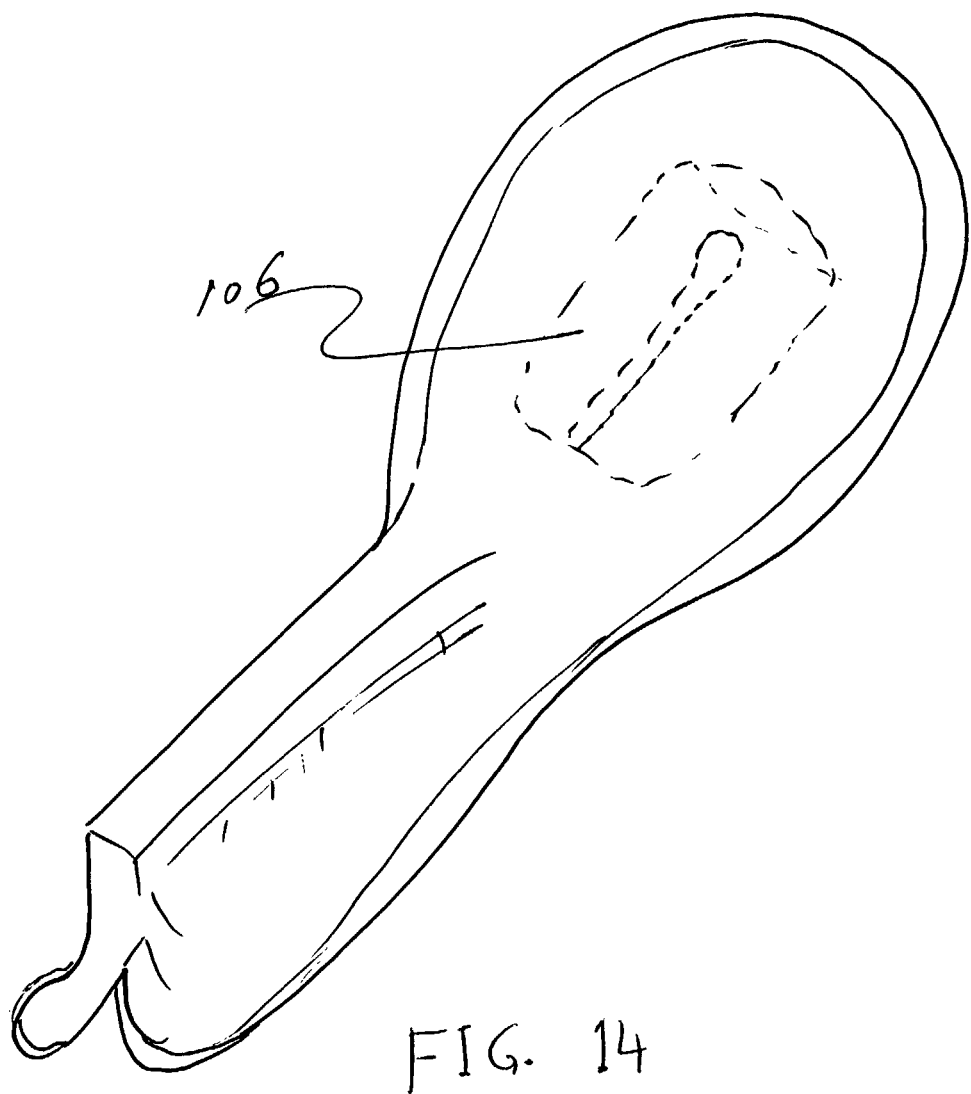
FIG. 14 is a perspective, schematic illustration of an integral or separate cosmetic crotch enhancer element showing the exaggerated pudendal cleft as still another embodiment on the garment faceable side of the sanitary napkin of FIG. 12.

FIG. 12 is a top plan view of another prior art related to the present invention where the inverted V-shape molds into the portion of the wearer's labia which is towards the buttocks, the perineum and the forward portion of wearer's buttocks which are towards the wearer' labia. FIG. 13 is a perspective, schematic illustration of an integral or separate cosmetic crotch enhancer element without the exaggerated pudendal cleft as item 105 on the garment faceable side of the sanitary napkin of FIG. 12. FIG. 14 is a perspective, schematic illustration of an integral or separate cosmetic crotch enhancer element with the exaggerated pudendal cleft as item 106 as still another embodiment on the garment faceable side of the sanitary napkin of FIG. 12.

Figure 15:
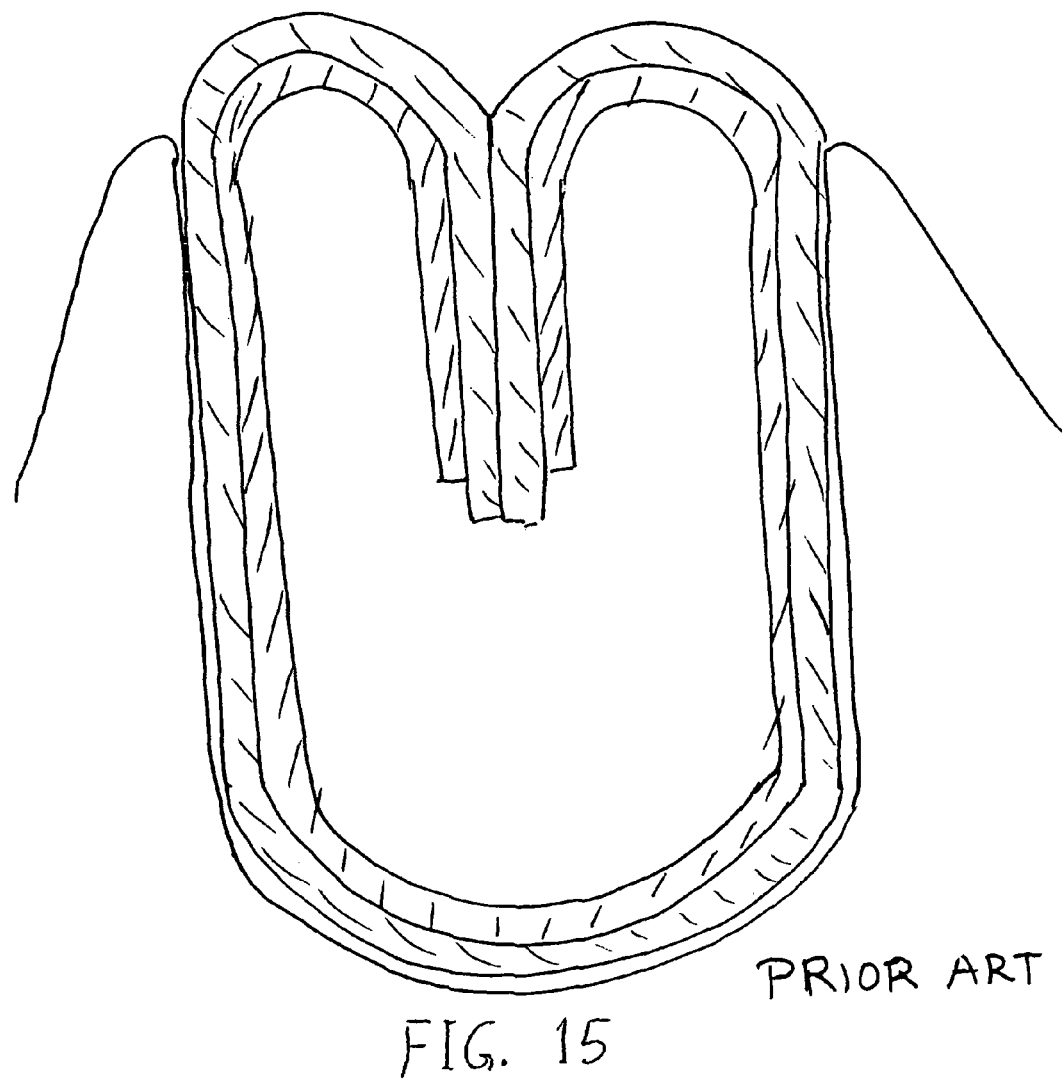
FIG. 15 is a cross-sectional view of an absorbent interlabial device of a prior art related to the present invention.
Figure 16:
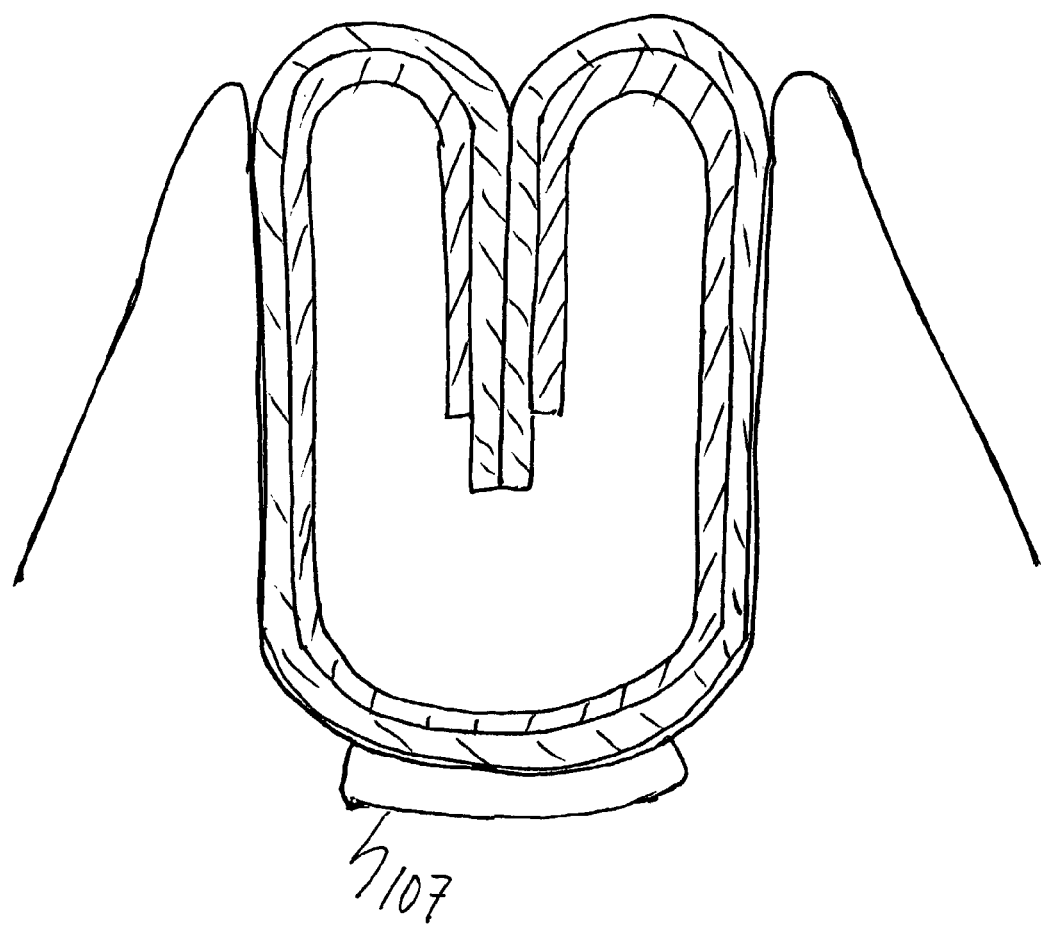
FIG. 16 is a cross-sectional view of an absorbent interlabial device with an integral or separate cosmetic crotch enhancer element without or with the exaggerated pudendal cleft as still another embodiment of the present invention.

FIG. 15 is a cross-sectional view of an absorbent interlabial device of a prior art related to the present invention. FIG. 16 is a cross-sectional view of an absorbent interlabial device with an integral or separate cosmetic crotch enhancer element with or without the exaggerated pudendal cleft as item 107 as still another embodiment of the present invention.

Figure 17:
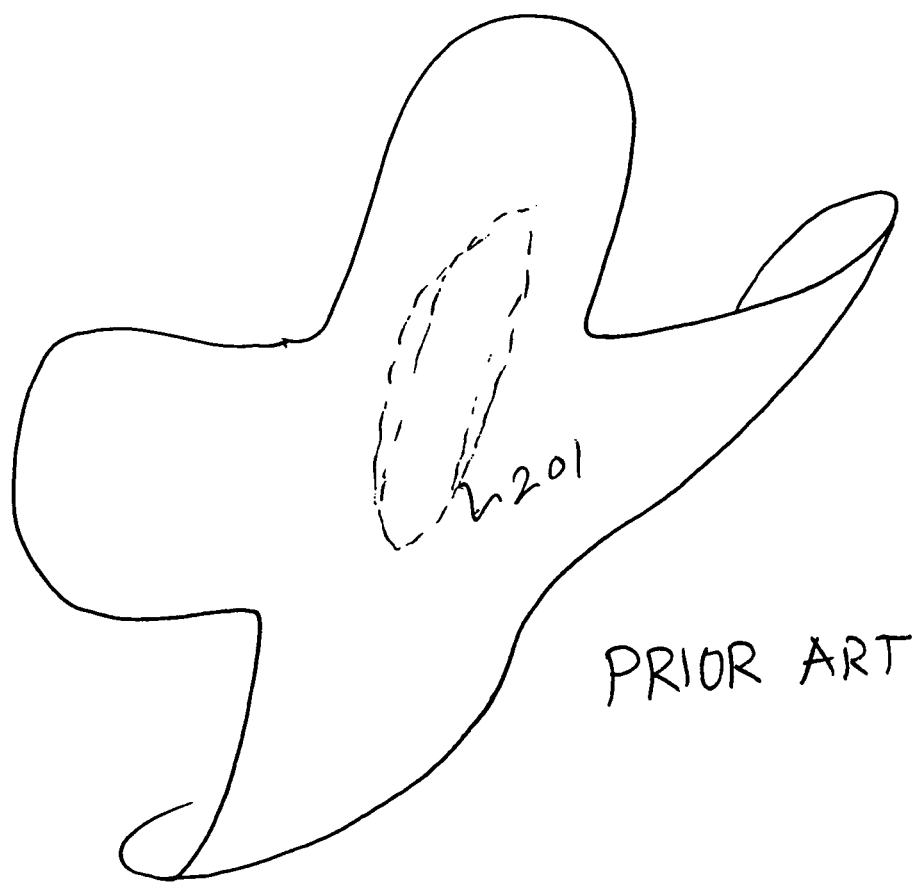
FIG. 17 is a perspective, schematic illustration of a prior art with absorbent longitudinal medial hump on the body faceable side of a sanitary napkin.
Figure 18:
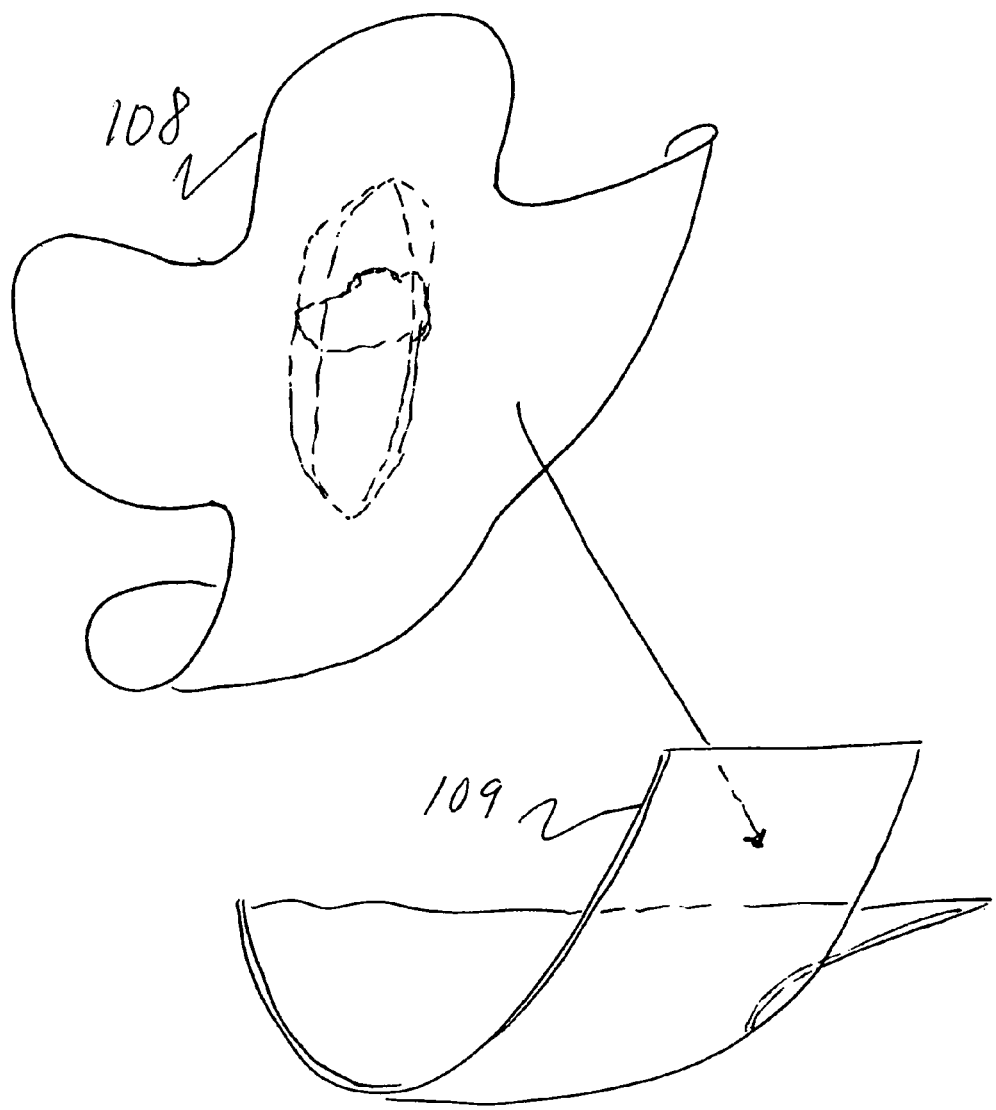
FIG. 18 is a perspective, schematic illustration of a prior art a sanitary napkin with absorbent longitudinal medial hump on it's body faceable side and placed onto the inner crotch portion of the undergarment.
Figure 19:
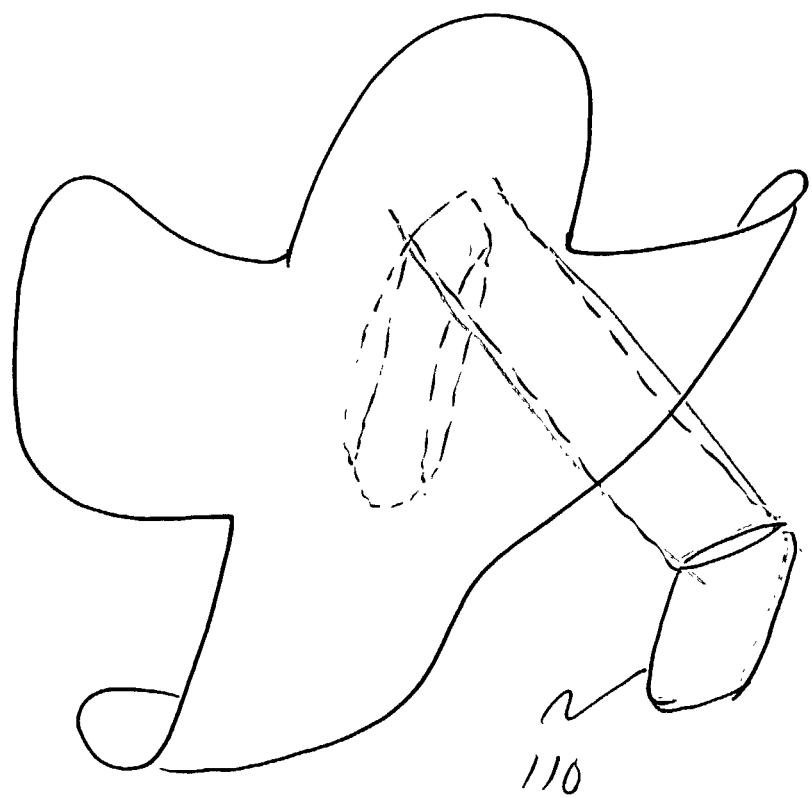
FIG. 19 is a perspective, schematic illustration of the placement of a separate cosmetic crotch enhancer element onto the garment faceable side of a conventional sanitary napkin with absorbent longitudinal medial hump on it's body faceable side.
Figure 20:
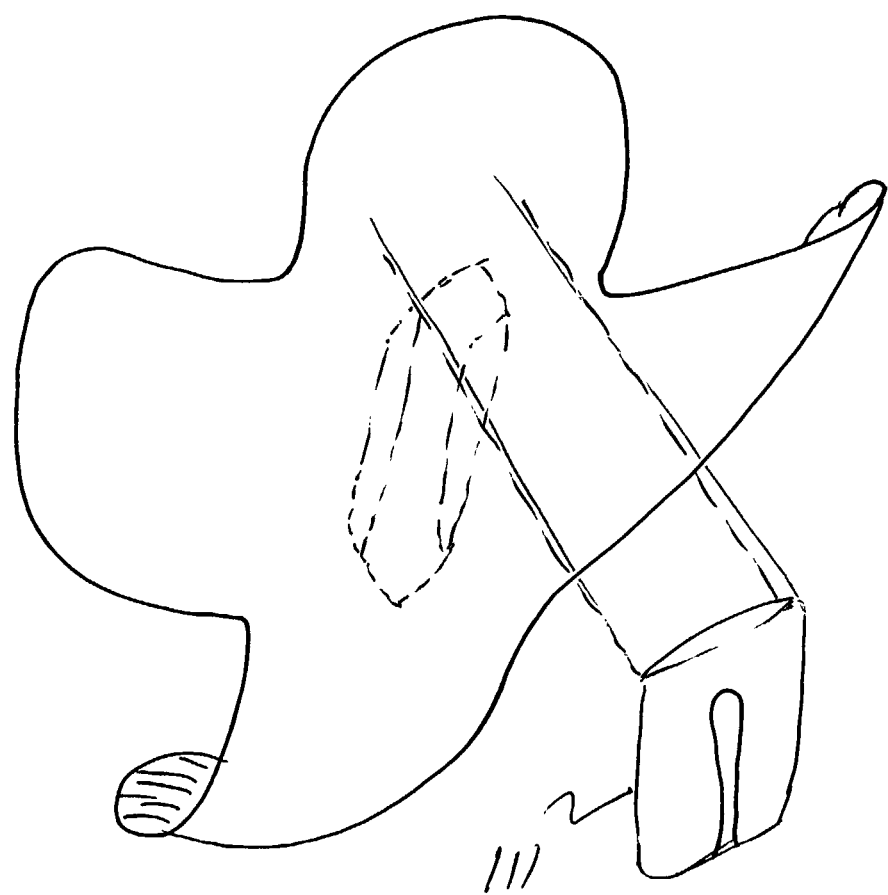
FIG. 20 is a perspective, schematic illustration of the placement of another embodiment of a separate cosmetic crotch enhancer element showing the exaggerated pudendal cleft onto the garment faceable side of a conventional sanitary napkin with absorbent longitudinal medial hump on it's body faceable side.
Figure 21:
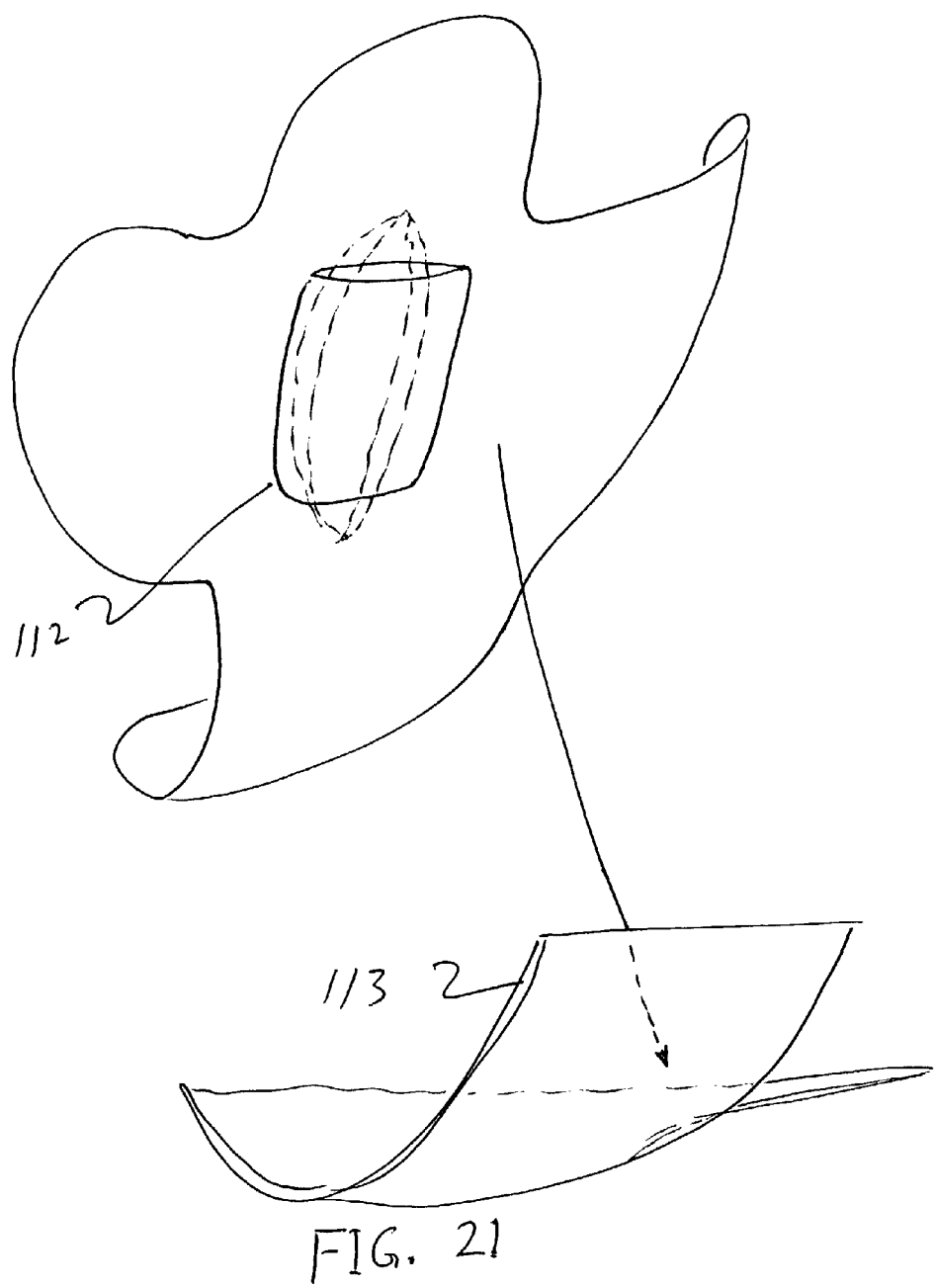
FIG. 21 is a perspective, schematic illustration of the placement of a sanitary napkin with absorbent longitudinal medial hump on it's body faceable side with an integral cosmetic crotch enhancer element onto the inner crotch portion of the undergarment.
Figure 22:
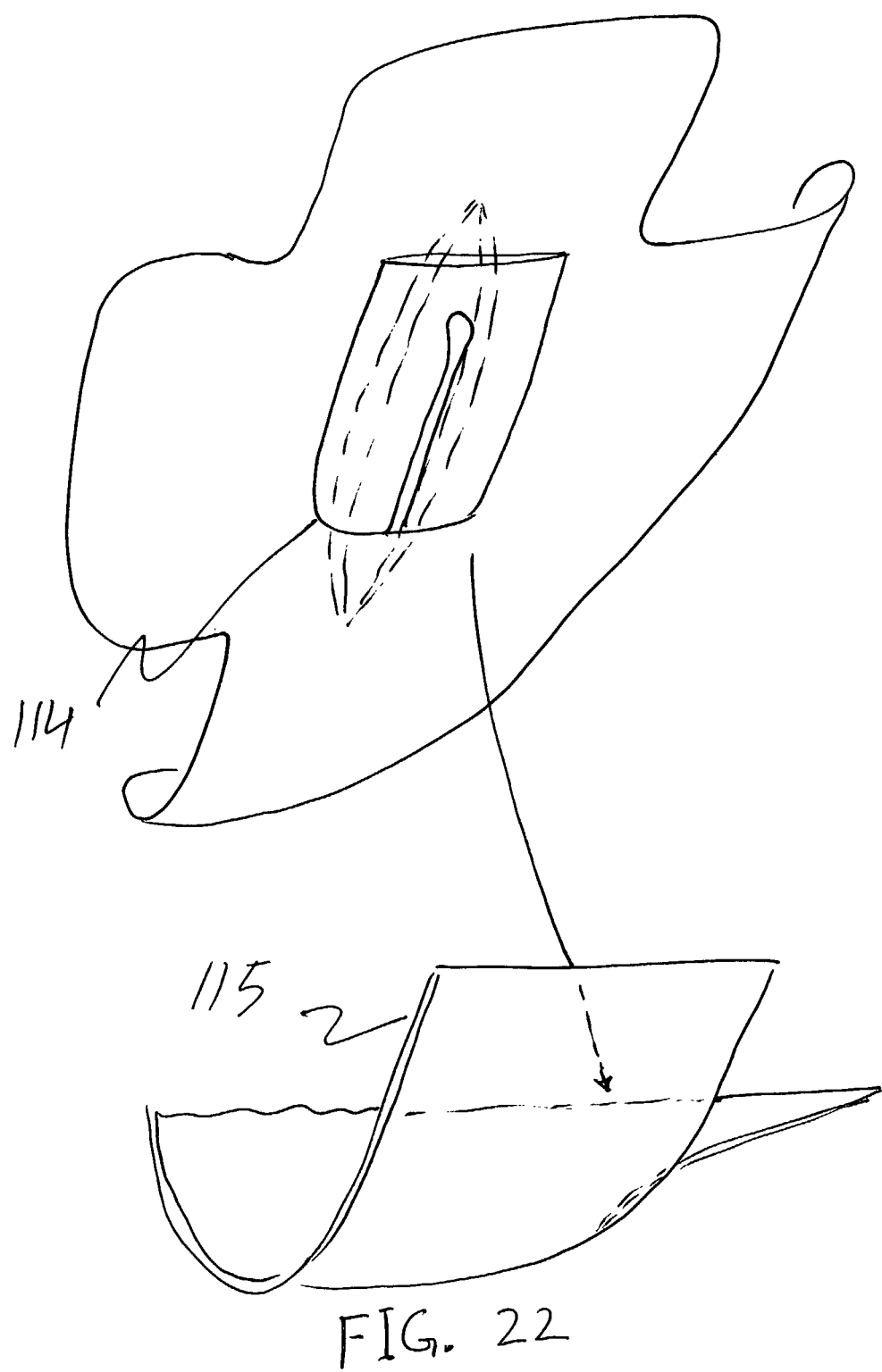
FIG. 22 is a perspective, schematic illustration of the placement of a sanitary napkin with absorbent longitudinal medial hump on it's body faceable side with another embodiment of an integral cosmetic crotch enhancer element showing the exaggerated pudendal cleft onto the inner crotch portion of the undergarment.

FIG. 17 is a perspective, schematic illustration of a prior art with absorbent longitudinal medial hump as item 201 on the body faceable side of a sanitary napkin. FIG. 18 is a perspective, schematic illustration of a prior art a sanitary napkin with absorbent longitudinal medial hump on it's body faceable side as item 108 and placed onto the inner crotch portion of the undergarment depicted as item 109. FIG. 19 is a perspective, schematic illustration of the placement of a separate cosmetic crotch enhancer element without exaggerated pudendal cleft as item 110 onto the garment faceable side of a conventional sanitary napkin with absorbent longitudinal medial hump on it's body faceable side. Item 110 may optionally have adhesive on the garment faceable side as well optionally on the sanitary napkin faceable side. The wearer may adjust the appropriate placement of item 110 so as to superimpose upon the human female wearer's authentic external genitalia or howsoever the wearer may desire for the personal or sexual expression of the wearer. FIG. 20 is a perspective, schematic illustration of the placement of another embodiment of a separate cosmetic crotch enhancer element with exaggerated pudendal cleft as item 111 onto the garment faceable side of a conventional sanitary napkin with absorbent longitudinal medial hump on it's body faceable side. Item 111 have optionally have adhesive on the garment faceable side as well optionally on it's sanitary faceable side. The wearer may adjust the appropriate placement of item 111 so as to superimpose upon the human female wearer's external genitalia or howsoever the wearer may desire for the personal or sexual expression of the wearer. FIG. 21 is a perspective, schematic illustration of the placement of a sanitary napkin with absorbent longitudinal medial hump on it's body faceable side with an integral cosmetic crotch enhancer element without the exaggerated pudendal cleft as item 112 onto the inner crotch portion of the undergarment depicted as item 113. Item 112 have optionally have adhesive on it's garment faceable side. FIG. 22 is a perspective, schematic illustration of the placement of a sanitary napkin with absorbent longitudinal medial hump on it's body faceable side with another embodiment of an integral cosmetic crotch enhancer element with exaggerated pudendal cleft as item 114 onto the inner crotch portion of the undergarment depicted as item 115. Item 114 may optionally have adhesive on it's garment faceable side.

Figure 23:
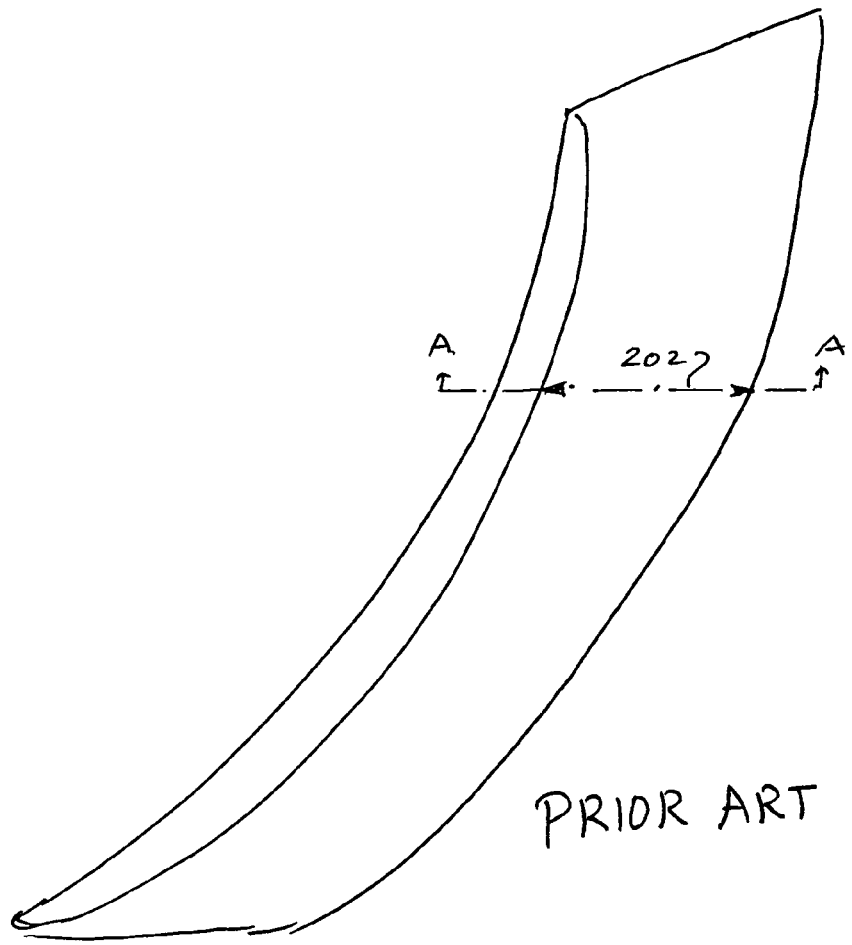
FIG. 23 is a perspective, schematic illustration of another prior art of a sanitary napkin without attachment flaps.
Figure 24:
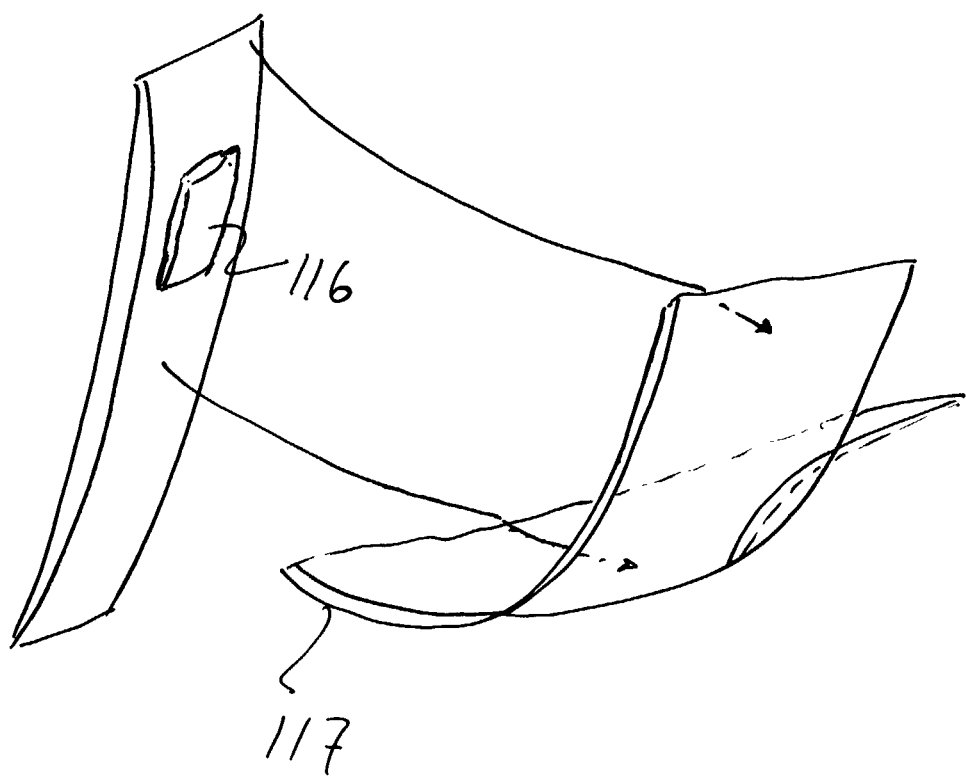
FIG. 24 is a perspective, schematic illustration of the placement of another embodiment of a sanitary napkin without attachment flaps with an integral cosmetic crotch enhancer element onto the inner crotch portion of the undergarment.
Figure 25:
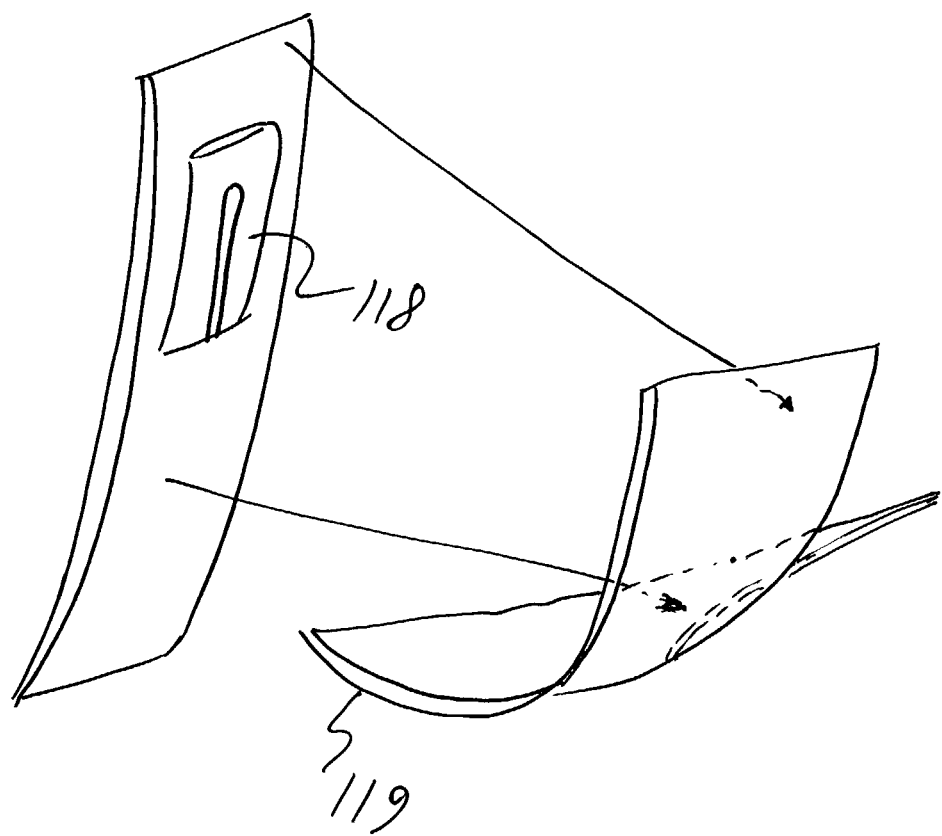
FIG. 25 is a perspective, schematic illustration of the placement of another embodiment of a sanitary napkin without attachment flaps with another embodiment of an integral cosmetic crotch enhancer element showing the exaggerated pudendal cleft onto the inner crotch portion of the undergarment.
Figure 26:
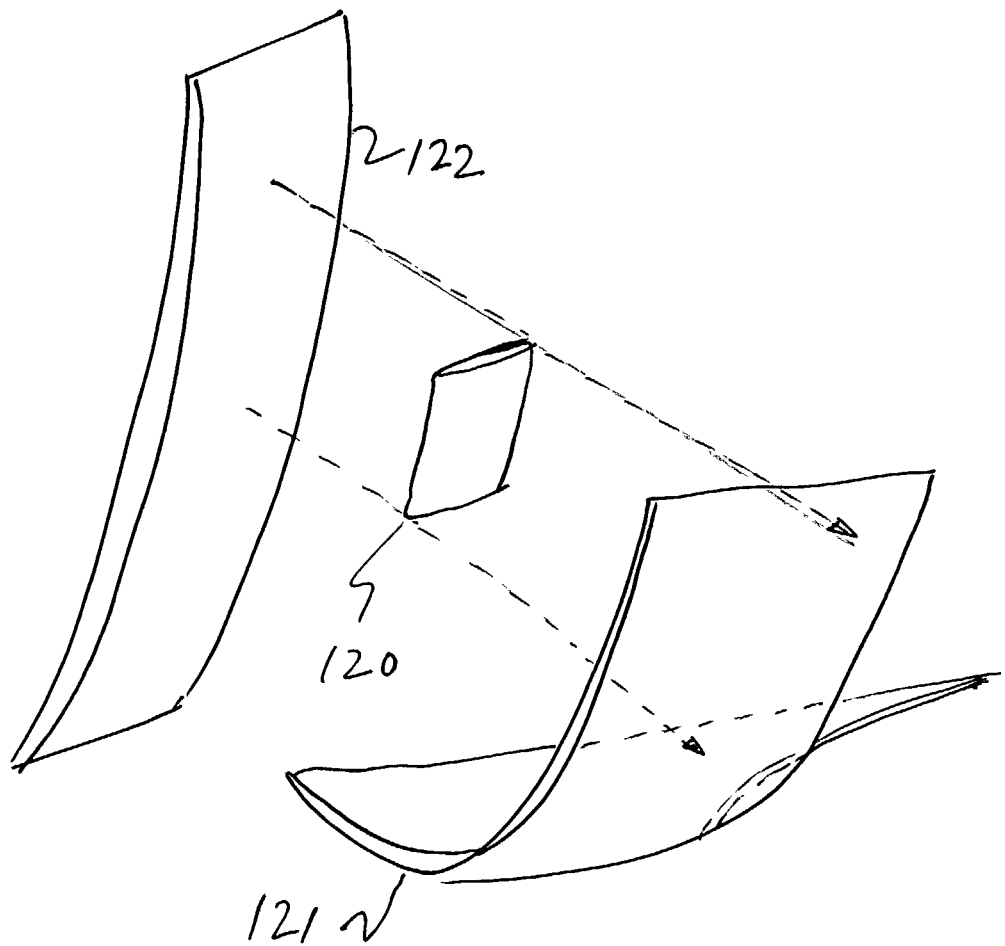
FIG. 26 is a perspective, schematic illustration of the placement of another embodiment of a conventional sanitary napkin without attachment flaps with a separate cosmetic crotch enhancer element onto the inner crotch portion of the undergarment.
Figure 27:
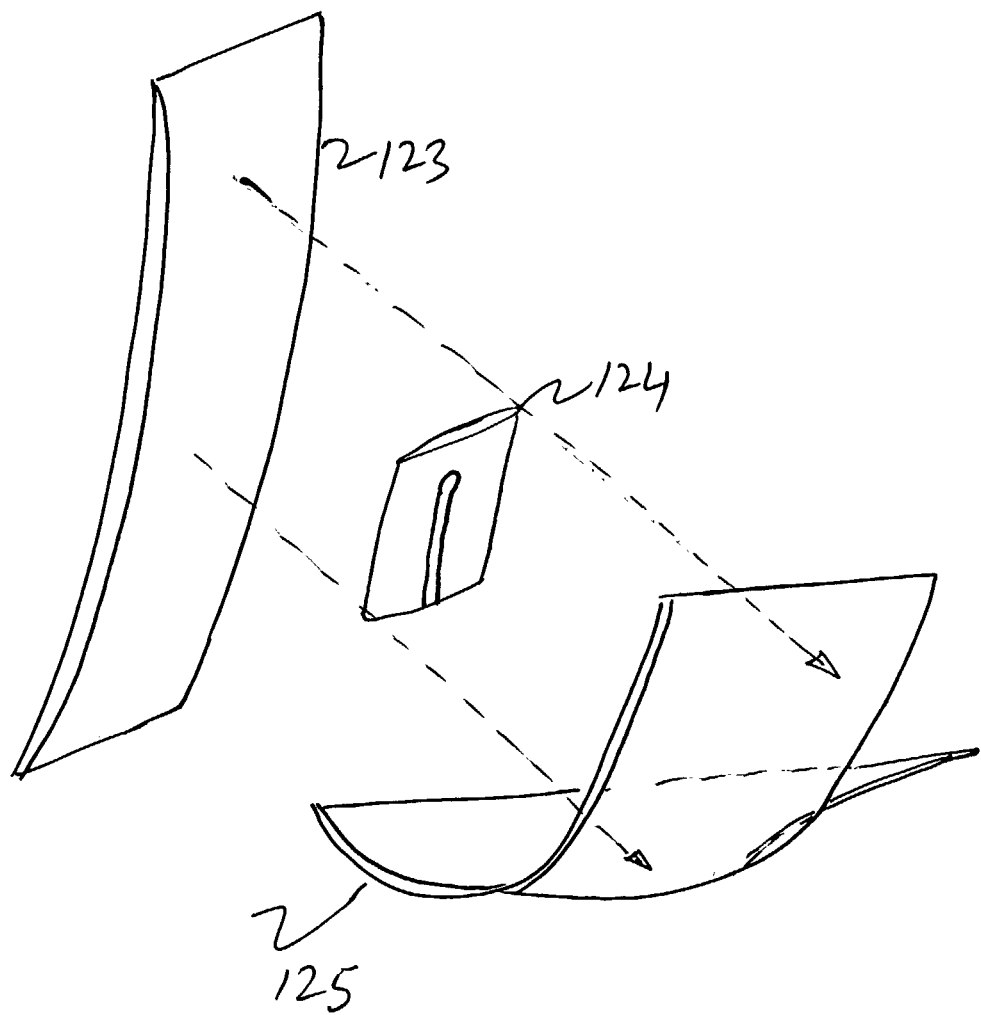
FIG. 27 is a perspective, schematic illustration of the placement of another embodiment of a conventional sanitary napkin without attachment flaps with another embodiment of a separate cosmetic crotch enhancer element showing the exaggerated pudendal cleft onto the inner crotch portion of the undergarment.

FIG. 23 is a perspective, schematic illustration of another prior art of a sanitary napkin without attachment flaps. Also shown is traverse medial width as item 202 of the absorbent article as per traverse line A-A. FIG. 24 is a perspective, schematic illustration of the placement of another embodiment of a sanitary napkin without attachment flaps with an integral cosmetic crotch enhancer element without the exaggerated pudendal cleft as item 116 onto the inner crotch portion of the undergarment depicted as item 117. Item 116 may optionally have adhesive on it's garment faceable side. FIG. 25 is a perspective, schematic illustration of the placement of another embodiment of a sanitary napkin without attachment flaps with another embodiment of an integral cosmetic crotch enhancer element with the exaggerated pudendal cleft as item 118 with optional adhesive on the garment faceable side of the item 118 onto the inner crotch portion of the undergarment depicted as item 119. Item 118 may optionally have adhesive on it's garment faceable side. FIG. 26 is a perspective, schematic illustration of the placement of another embodiment of a conventional sanitary napkin without attachment flaps as item 122 with a separate cosmetic crotch enhancer element without the exaggerated pudendal cleft as item 120 with optional adhesive on the garment faceable side of the item 120 onto the inner crotch portion of the undergarment depicted as item 121. The wearer may adjust the appropriate placement of item 120 so as to superimpose upon the human female wearer's authentic external genitalia or howsoever the wearer may desire for the personal or sexual expression of the wearer. FIG. 27 is a perspective, schematic illustration of the placement of another embodiment of a conventional sanitary napkin without attachment flaps as item 123 with another embodiment of a separate cosmetic crotch enhancer element with the exaggerated pudendal cleft as item 124 with optional adhesive on the garment faceable side of item 124 onto the inner crotch portion of the undergarment depicted as item 125. The wearer may adjust the appropriate placement of item 124 so as to superimpose upon the human female wearer's authentic external genitalia or howsoever the wearer may desire for the personal or sexual expression of the wearer.

Figure 28:
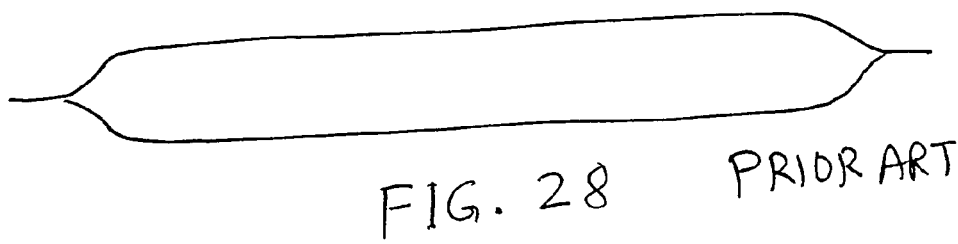
FIG. 28 is a cross-sectional view taken along longitude of FIG. 23.
Figure 29:
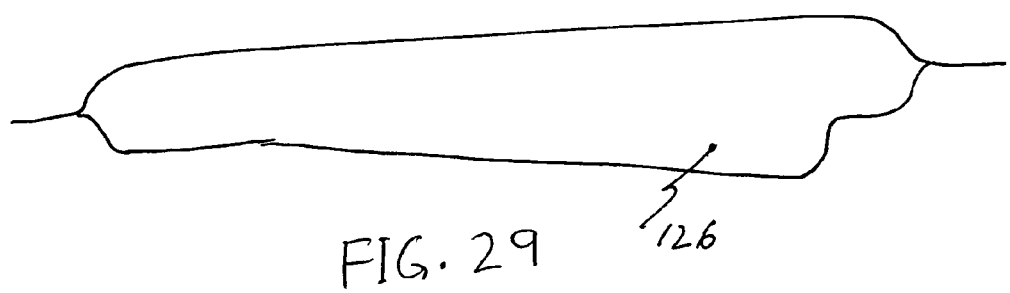
FIG. 29 is a cross-sectional view taken along longitude of the sanitary napkin without attachment flaps and integral cosmetic crotch enhancer element of FIG. 24 or FIG. 25 illustrating the increased volume of the absorbent due to the cosmetic crotch enhancer element.
Figure 30:
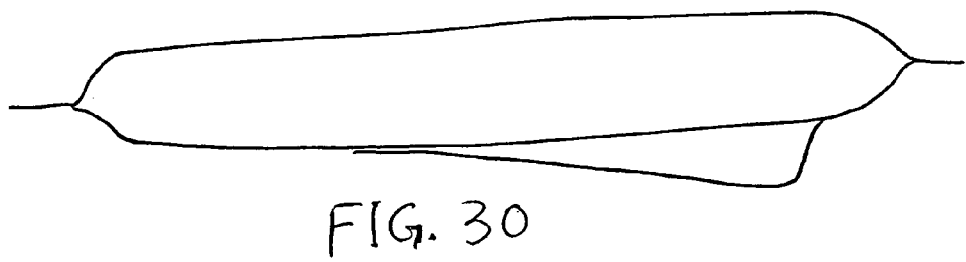
FIG. 30 is a cross-sectional view taken along longitude of the sanitary napkin without attachment flaps and integral cosmetic crotch enhancer element of FIG. 24 or FIG. 25 when the integral cosmetic crotch enhancer element does not result in increased volume of the absorbent of the sanitary napkin.

FIG. 28 is a cross-sectional view taken along the longitude of FIG. 23. FIG. 29 is a cross-sectional view taken along longitude of the sanitary napkin without attachment flaps and integral cosmetic crotch enhancer element of FIG. 24 or FIG. 25 illustrating the increased volume of the absorbent due to the cosmetic crotch enhancer element as item 126. FIG. 30 is a cross-sectional view taken along longitude of the sanitary napkin without attachment flaps and integral cosmetic crotch enhancer element of FIG. 24 or FIG. 25 when the integral cosmetic crotch enhancer element does not result in increased volume of the absorbent of the sanitary napkin.

It is suggested that the human female wearer of the absorbent article of this invention will take normal precautions and responsible usage and safety to protect from undesirable or unwanted situations.

The cosmetic human female crotch enhancer element may be any absorbent material that is capable of absorbing or retaining excretions from the human female genitalia. The absorbent material may be a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combination of materials, or mixtures of these. The absorbent material may also partially comprise less absorbent or non-absorbent material, such as polyurethane foam, which when combined with absorbent material (such as absorbent gelling materials), can be formed into suitable absorbent structures. Preferred absorbent materials are those mentioned above that are wet and dry resilient and can be formed into a resilient structure. Some absorbent foam materials are made from high internal phase emulsions, and are known as "HIPE" foams. Suitable HIPE absorbent foams are described in U.S. Pat. No. 5,260,345 issued to DesMarais, et al. on Nov. 9, 1993; U.S. Pat. No. 5,268,224 issued to DesMarais, et al. on Dec. 7, 1993; U.S. Pat. No. 5,387,207 issued to Dyer, et al. on Feb. 7, 1995; U.S. Pat. No. 5,550,167 issued to DesMarais on Aug. 27, 1996; U.S. Pat. No. 5,563,179 issued to Stone, et al. on Oct. 8, 1996; U.S. Pat. No. 5,650,222 issued to DesMarais, et al. on Jul. 22, 1997; and allowed U.S. patent application Ser. No. 08/542,497 filed Oct. 13, 1995, by Dyer. These patents may be referred to herein as the "Absorbent Foam Material" patents. Such absorbent foam materials are particularly preferred because they can be provided with good resistance to compression and resiliency following compression. Further, the cosmetic human female crotch enhancer element may be any less absorbent or non-absorbent material but not limited to polyurethane foam, particularly when the cosmetic human female crotch enhancer element does not provide any absorbent volume associated with it's contours and curves.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

It should be understood that the foregoing description is only illustrative of the invention. Various alternatives and modifications can be devised, without departing from the spirit and scope of the invention.

What is claimed is:

1. An absorbent article in the form of a sanitary napkin, panty liner, or incontinence pad, having a wearer-facing side and a garment-facing side; and
   a cosmetic female crotch enhancer element positioned on the garment-facing side of the absorbent article, wherein said cosmetic female crotch enhancer element has the appearance of labia majora, labia minora, clitoris, and clitoral hood of female genitalia.

2. The absorbent article of claim 1, wherein said cosmetic female crotch enhancer element is a monolithic part of the absorbent article.

3. The absorbent article of claim 1, wherein said cosmetic female crotch enhancer element is adhesively attached to the garment-facing side of the absorbent article.

4. The absorbent article of claim 1, wherein said cosmetic female crotch enhancer element comprises adhesive on a garment-facing surface thereof, the adhesive being configured to attach the cosmetic female crotch enhancer element to a user's undergarment.

5. The absorbent article of claim 1, wherein said cosmetic female crotch enhancer element is capable of being positioned adjacent a user's genitalia.

6. The absorbent article of claim 1, further comprising adhesive on said garment-facing side.

7. The absorbent article of claim 1, further comprising side flaps with adhesive thereon.

* * * * *